United States Patent
Kataoka et al.

(10) Patent No.: US 6,232,057 B1
(45) Date of Patent: May 15, 2001

(54) IODIDE ION RELEASING COMPOUND, AND SILVER HALIDE LIGHT-SENSITIVE PHOTOGRAPHIC MATERIAL CONTAINING THE SAME

(75) Inventors: Emiko Kataoka; Norio Miura, both of Hino (JP)

(73) Assignee: Konica Corporation (JP)

( * ) Notice: Subject to any disclaimer, the term of this patent is extended or adjusted under 35 U.S.C. 154(b) by 0 days.

(21) Appl. No.: 09/217,704

(22) Filed: Dec. 21, 1998

(30) Foreign Application Priority Data

Dec. 22, 1997 (JP) .................................... 9-365573

(51) Int. Cl.[7] ........................................ G03C 1/08
(52) U.S. Cl. ........................................ 430/567; 430/569
(58) Field of Search .................... 430/567, 569

(56) References Cited

U.S. PATENT DOCUMENTS

| | | | |
|---|---|---|---|
| 5,482,826 | * | 1/1996 | Okamura et al. ............ 430/569 |
| 5,527,664 | * | 6/1996 | Kikuchi et al. ............. 430/569 |

FOREIGN PATENT DOCUMENTS

| | | | |
|---|---|---|---|
| 412699 | 7/1922 | (DE) . | |
| 0563701 | 10/1993 | (EP) | ............... G03C/1/005 |
| 2278333 | 2/1976 | (FR) | ............... A61K/31/195 |

OTHER PUBLICATIONS

Baker, B.R. et al.—"Potential anticancer agents"—Journal of Organic Chemistry, 1962, pp. 3283–3295.
Bergel, et al.—"Aryl–2–halogenoalkylamines"—Journal of the Chemical Society, 1955, pp. 3835–3839.
Cambanis, Gericke—"Aromatische N–LOST–Verbindungen"—Arzneimittel–Forschung, vol. 25, 1975, pp. 1–9.
European Search Report EP 98 12 4290.

* cited by examiner

Primary Examiner—Hoa Van Le
(74) Attorney, Agent, or Firm—Jordan B. Bierman; Bierman, Muserlian and Lucas

(57) ABSTRACT

An iodide ion releasing compound represented by the following Formula [1],

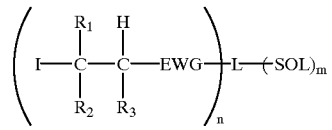

Formula [1]

wherein $R_1$, $R_2$ and $R_3$ represent a hydrogen atom and substituents; EWG represents $-CO_2-$, $-OCO-$, $-SO_2-$, $-SO_2O-$, $-OSO_2-$, $-CONR_4-$, $-NR_5CO-$, $-CSNR_6-$, $-NR_7CS-$, $-NR_8-$, $-O-$, $-S-$, $-CO-$, $-COCO-$ and $-NR_9SO_2-$; L represents linking group and SOL represents aqueous soluble group; $R_4$, $R_5$, $R_6$, $R_7$, $R_8$ and $R_9$ represent a hydrogen atom and substituents; n and m represent an integer of 1–4.

8 Claims, No Drawings

US 6,232,057 B1

IODIDE ION RELEASING COMPOUND, AND SILVER HALIDE LIGHT-SENSITIVE PHOTOGRAPHIC MATERIAL CONTAINING THE SAME

FIELD OF THE INVENTION

The present invention relates to a novel iodide ion releasing compound and a silver halide light-sensitive photographic material employing the same, especially a silver halide light-sensitive photographic material exhibits an excellent property in sensitivity and fog.

BACKGROUND OF THE INVENTION

Recently, along with the increased popularity of picture-taking instruments such as cameras, there increase picture-taking chances by use of a silver halide light sensitive photographic material (hereinafter, referred to as a photographic material). As a result, further enhancement in sensitivity and image quality has been desired by the public.

One domain ant factor for enhancing sensitivity and image quality of the photographic material concerns silver halide grains, and there has been on going development of silver halide grains aimed at enhancement of sensitivity and image quality.

Japanese Patent Publication Open to Public inspection (hereinafter referred to as JP-A) Nos. 5-323487, 6-11781, 6-11782, 6-27567, 6-250309, 6-250310, 6-250311, 6-250313, 6-242527 etc. disclose the realization of enhancement of sensitivity and the improvement of fog-pressure-resistance by using the iodide ion releasing compound in preparing a silver halide grain.

However, since the releasing speed of iodide ion from these well-known iodide ion releasing compounds is slow, there has been limitation in enhancement of sensitivity and it is insufficient with these compounds to meet recent demand in the photographic material and development of more skilled know-how in the photographic material has been desired.

SUMMARY OF THE INVENTION

An object of the present invention is to provide the photographic material achieving enhanced sensitivity and reduced fog using iodide ion releasing compound which can release the iodide ion rapidly.

DETAILED DESCRIPTION OF THE INVENTION

Above object of the invention could be attained by the following method.

(1) An iodide ion releasing compound represented by the following Formula [1],

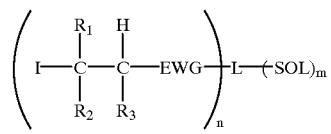

Formula [1]

wherein $R_1$, $R_2$ and $R_3$ represent a hydrogen atom and substituents; EWG represents —$CO_2$—, —OCO—, —$SO_2$—, —$SO_2O$—, —$OSO_2$—, —$CONR_4$—, —$NR_5CO$—, —$CSNR_6$—, —$NR_7CS$—, —$NR_8$—, —O—, —S—, —CO—, —COCO— and —$NR_9SO_2$—; L represents linking group; SOL represents aqueous soluble group; $R_4$, $R_5$, $R_6$, $R_7$, $R_8$ and $R_9$ represent a hydrogen atom and substituents; n and m represent an integer of 1–4.

(2) The iodide ion releasing compound of item 1, wherein EWG represents —$SO_2$—.

(3) A silver halide grain formed using at least one of an iodide ion releasing compound represented by the following Formula [1],

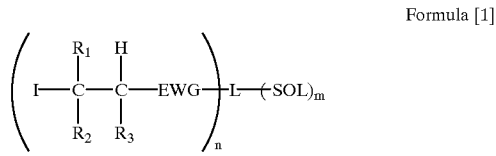

Formula [1]

wherein $R_1$, $R_2$ and $R_3$ represent a hydrogen atom and substituents, EWG represents —$CO_2$—, —OCO—, —$SO_2$—, —$SO_2O$—, —$OSO_2$—, —$CONR_4$—, —$NR_5CO$—, —$CSNR_6$—, —$NR_7CS$—, —$NR_8$—, —O—, —S—, —CO—, —COCO— and —$NR_9SO_2$—, L represents an aromatic group and a heterocyclic group and SOL represents aqueous soluble group; $R_4$, $R_5$, $R_6$, $R_7$, $R_8$ and $R_9$ represent a hydrogen atom and substituents; n and m represent an integer of 1–4.

(4) The iodide ion releasing compound of item 3, wherein EWG represents —$SO_2$—.

(5) A silver halide photographic light-sensitive material containing at least one of the silver halide grain formed using at least one of an iodide ion raleasing compound represented by the following Formula [1],

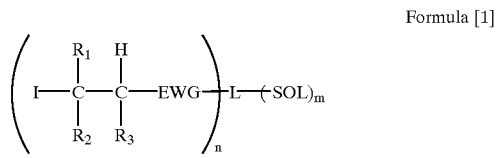

Formula [1]

wherein $R_1$, $R_2$ and $R_3$ represent a hydrogen atom and substituents, EWG represents —$CO_2$—, —OCO—, —$SO_2$—, —$SO_2O$—, —$OSO_2$—, —$CONR_4$—, —$NR_5CO$—, —$CSNR_6$—, —$NR_7CS$—, —$NR_8$—, —O—, —S—, —CO—, —COCO— and —$NR_9SO_2$—, L represents an aromatic group and a heterocyclic group and SOL represents aqueous soluble group; $R_4$, $R_5$, $R_6$, $R_7$, $R_8$ and $R_9$ represent a hydrogen atom and substituents; n and m represent an integer of 1–4.

(6) The iodide ion releasing compound of item 5, wherein EWG represents —$SO_2$—.

Next, the invention will be explained in detail

In the formula [1], $R_1$, $R_2$ and $R_3$ represent a hydrogen atom and substituents, and as a preferable substituent is cited an alkyl group (for example, a methyl group, an ethyl group and an iso-propyl group), a cyano group, a nitro group, an alkoxy group (for example, a methoxy group And an ethoxy group). $R_4$, $R_5$, $R_6$, $R_7$, $R_8$ and $R_9$ represent a hydrogen atom and substituents and as a preferable substituent is cited an alkyl group (for example, a methyl group, an ethyl group and an isopropyl group). A linking group represented by L represents an aromatic group and a heterocyclic group, and as an aromatic group is cited a phenyl group and a naphthyl group, and as a heterocyclic group is cited a pyridine ring, a pyridazine ring, a pyrimidine ring, a pyrazine ring, a triazine ring and an oxazole ring. These groups cited above may possess sustitutents. As preferable sustitutents are cited an alkyl group (for example, a methyl group, an ethyl group, an isopropyl group and a cyclohexyl group), a cyano group, a nitro group, an amino group, an alkoxy group (for example, a methoxy group and an ethoxy group) and a halogen atom (for example, a chlorine, a bromine and an iodine atom). An aqueous group represented by SOL concretely represents —OM, —COOM, —SO₃M, —PO₃M and a quaternary onium salt and M represents a hydrogen and an alkali metal. The preferable aqueous groups are —COOM and —SO₃M.
The example of the compound represented by formula [1] in the invention is listed below, but is not limited thereto.
1)
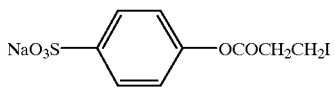
2)
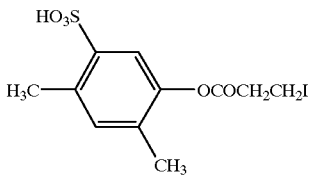
3)
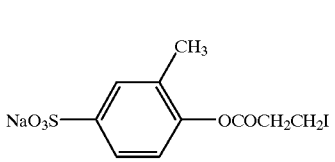
4)
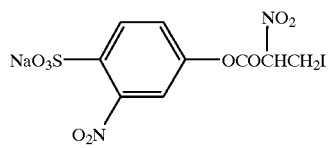
5)
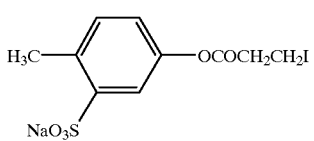
6)
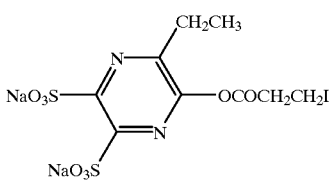
7)
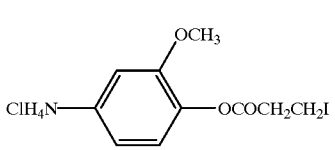
8)
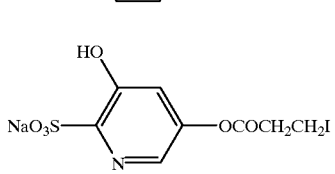
9)
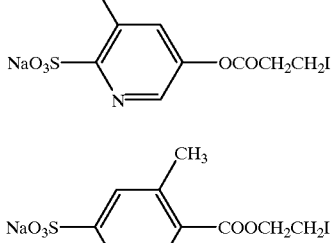
-continued
10)
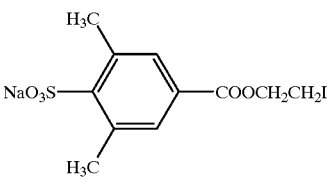
11)
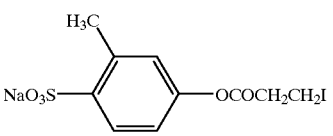
12)
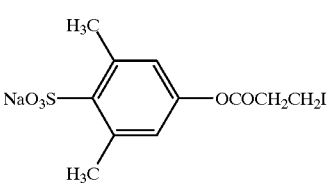
13)
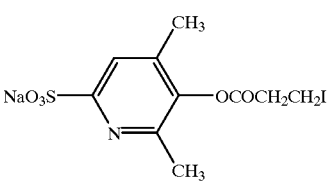
14)
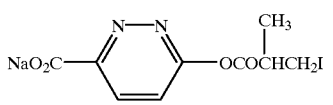
15)
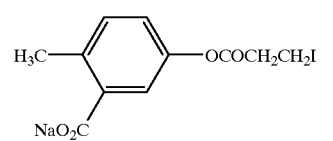
16)
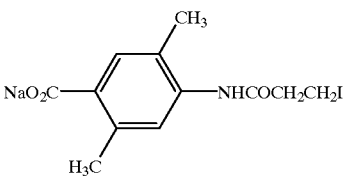
17)
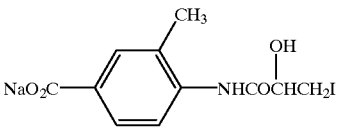
18)
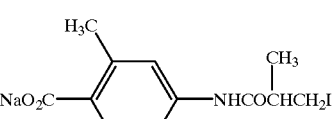

19) 2-methyl-4-(sodiosulfo)-N-(2-iodoethyl)benzamide structure
20) 3-methyl-4-(sodiosulfo)-N-(1-methyl-2-iodoethyl)benzamide structure
21) 2,4-dimethyl-5-(sodiosulfo)-N-(2-iodoethyl)aniline amide structure
22) 4,6-dimethyl-5-(sodiosulfo)-N-(1-methoxy-2-iodoethyl)pyridine-2-carboxamide structure
23) 2,6-dimethyl-4-(sodiosulfo)-N-(2-iodoethyl)aniline amide structure
24) 6-methoxy-5-(sodiosulfo)-N-(2-iodoethyl)pyrazine-2-amine amide structure
25) 2-hydroxy-4-methyl-5-(sodiocarboxy)-N-(2-iodoethyl)aniline amide structure
26) 2-ethyl-4-(sodiocarboxy)-N-(2-iodoethyl)aniline amide structure
27) 5-methyl-3-(sodiocarboxy)-N-(2-iodoethyl)-1,2,4-triazine-6-amine amide structure
28) 2-methyl-4-NHCOCH₂CH₂I-benzoic acid structure
29) 2-methyl-4-(sodiosulfo)-N-(2-iodoethyl)benzamide structure
30) 3-methyl-4-(sodiosulfo)-N-(2-iodoethyl)benzamide structure
31) 4-(sodiosulfo)-N-(2-iodoethyl)aniline amide structure
32) 4-methyl-3-(sodiosulfo)-N-(2-iodoethyl)aniline amide structure
33) 2,5-dimethyl-4-(sodiosulfo)-N-(2-iodoethyl)aniline amide structure
34) 2-methyl-4-(sodiosulfo)-N-(2-iodoethyl)aniline amide structure
35) 3-methyl-4-(sodiosulfo)-N-(2-iodoethyl)aniline amide structure
36) 2-ethyl-4-(sodiosulfo)-N-(1-methyl-2-iodoethyl)benzamide structure
37) 2-methyl-5-methoxy-4-(sodiosulfo)-N-(2-iodoethyl)aniline amide structure -continued
38) 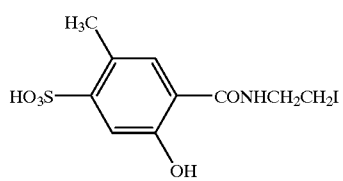
39) 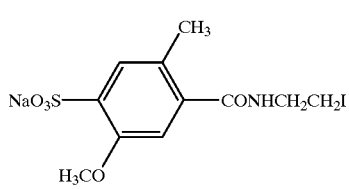
40) 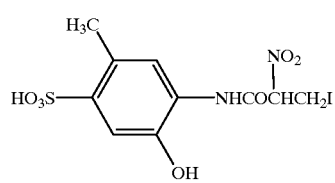
41) 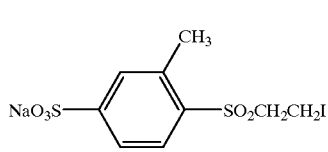
42) 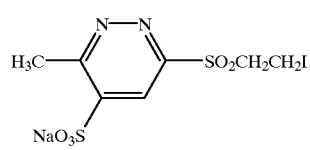
43) 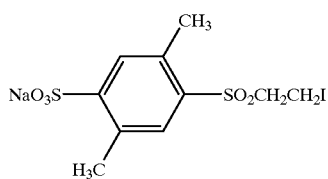
44) 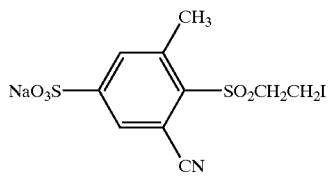
45) 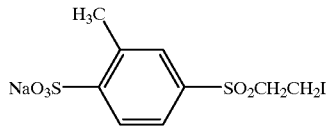
46) 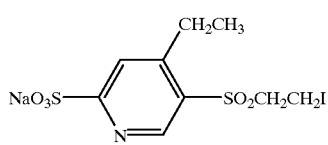
-continued
47) 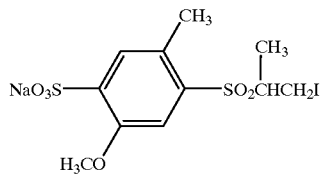
48) 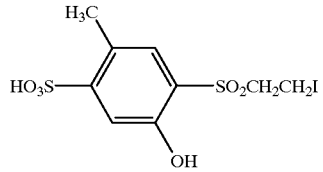
49) 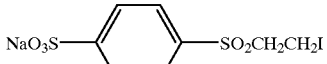
50) 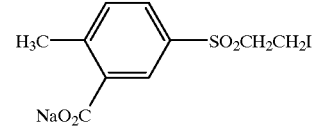
51) 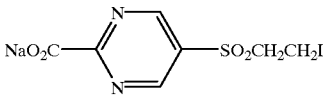
52) 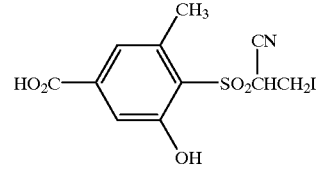
53) 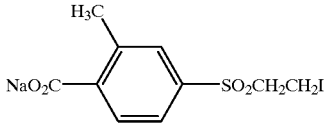
54) 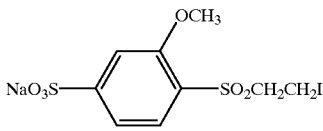
55) 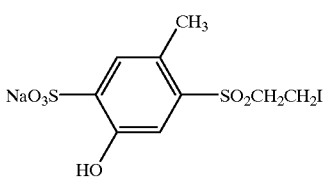

56) 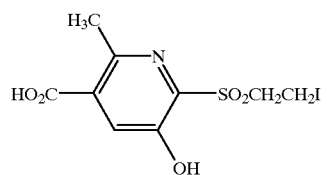
57) 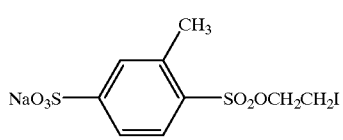
58) 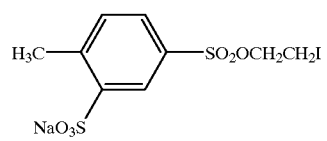
59) 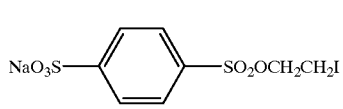
60) 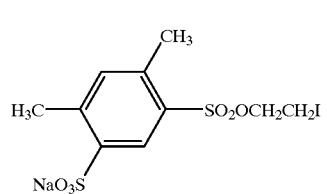
61) 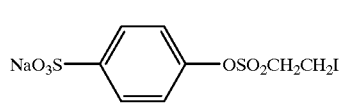
62) 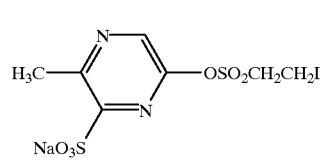
63) 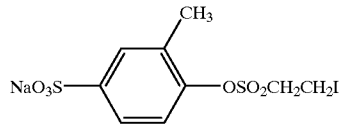
64) 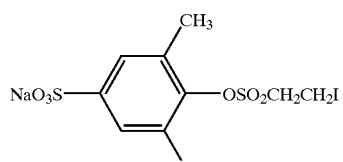
65) 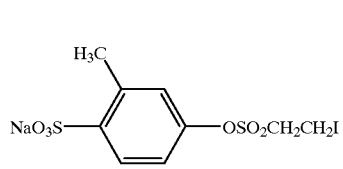
66) 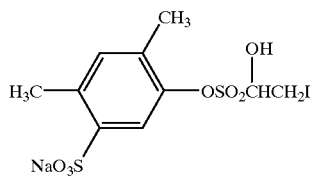
67) 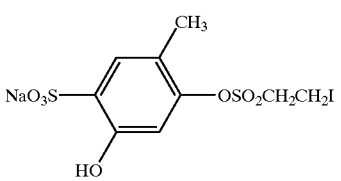
68) 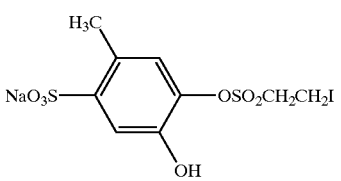
69) 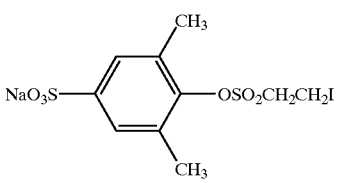
70) 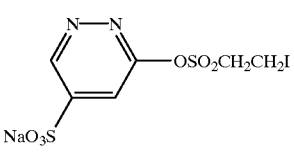
71) 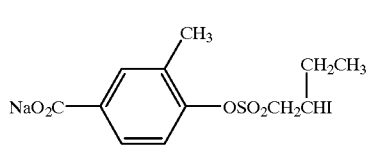
72) 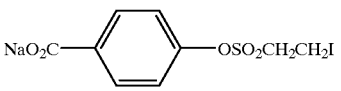
73) 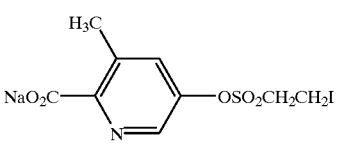
74) 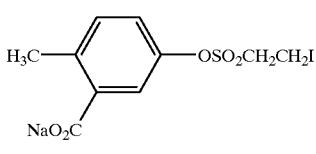

75) 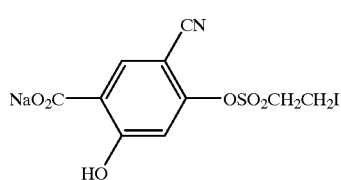
76) 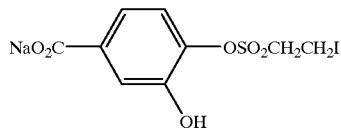
77) 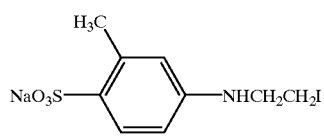
78) 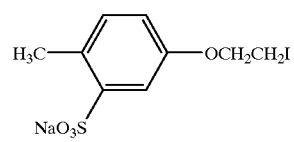
79) 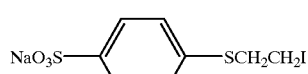
80) 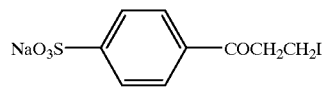
81) 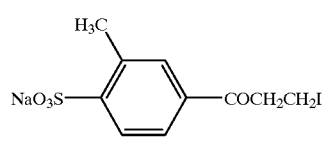
82) 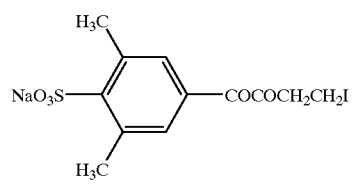
83) 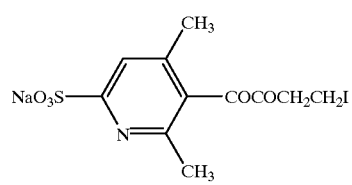
84) 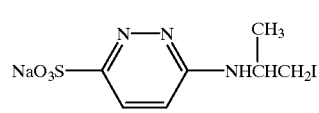
85) 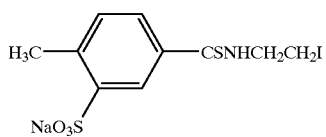
86) 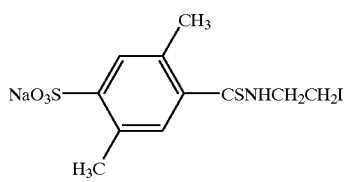
87) 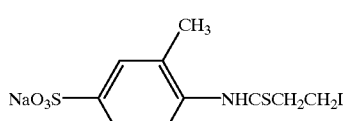
88) 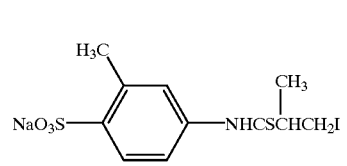
89) 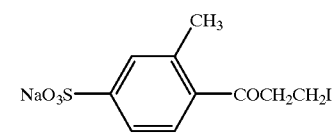
90) 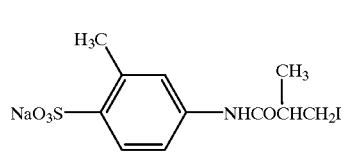
91) 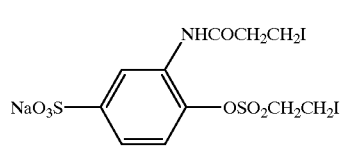
92) 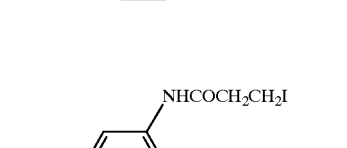
93) 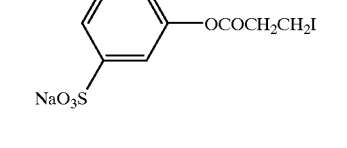

-continued

94) 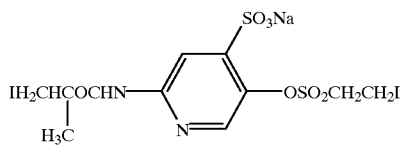

95) 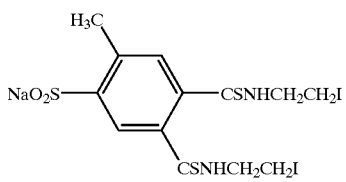

96) 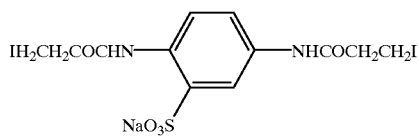

97) 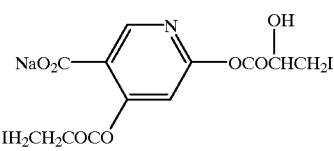

98) 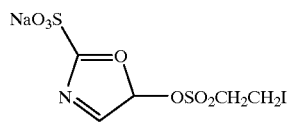

99) 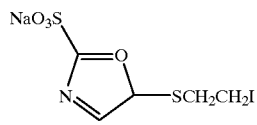

The compound represented by the formula [I] of the invention can be synthesized by a known substitution reaction. For example, are used the reaction methods as shown in the following chemical formulas.

[A]—OH+[B]COCl→base→[A]—OCO—[B]+HCl:  Formula 1

[A]—NH₂+[B]—COCl→base→[A]—NHCO—[B]+HCl: Formula 2

[A]—OH+[B]—SO₂Cl→base→[A]—OSO₂—[B]+HCl: Formula 3

[A] represents an aromatic group, and [B] represents an aliphatic group.

The synthetic methods for obtaining the representative compounds are sown below.

SYNTHETIC EXAMPLE 1
(Synthesis of an exemplified Compound 1)

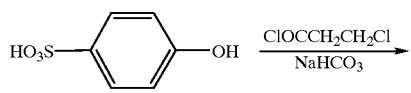

-continued

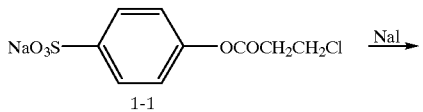

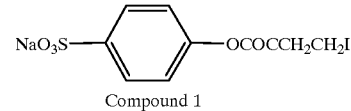

Compound 1

130 g of phenol sulfonic acid was dissolved in 1000 ml of water and 140 g of sodium hydrogencarbonate was added little by little to the above obtained solution. The mixture was cooled at 10° C. after adding sodium hydrogencarbonate, then 114 g of chloropropionic acid chloride was slowly added to the mixture. After adding chloropropionic acid chloride, the reaction temperature of the mixture was heated up to room temperature and stirred for 2 hours. After 30 g of active carbon was added and stirred still more, the active carbon was removed by filtration and filtrated solution was evaporated under a reduced pressure. The residue was recrystallized from water and thus 122 g (a yield of 62%) of compound (1-1) was obtained. 100 g of the compound (1-1) was dissolved in 800 ml of water and to this solution was added 400 g of sodium iodide. After then, the mixture was heated up to 60° C. and stirred for 3 hours. After the reaction, water was removed by evaporation under a reduced pressure. The residue was recrystallized from water and thus 104 g (a yield of 73%) of the exemplified Compound 1 was obtained and the chemical structure of thus obtained exemplified Compound 1 was confirmed by NMR and mass-spectrum thereof.

SYNTHETIC EXAMPLE 2
(Synthesis of an exemplified Compound 31)

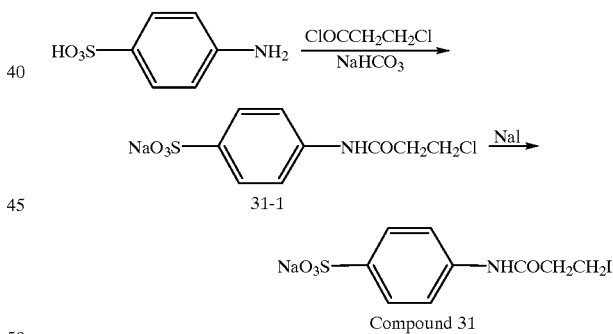

Compound 31

131.8 g of sulfanilic acid was dissolved in 1000 ml of water and 143.2 g of sodium hydrogencarbonate was added little by little to the above obtained solution. The mixture was cooled at 10° C. after adding sodium hydrogencarbonate, then 109 g of chloropropionic acid chloride was slowly added to the mixture. After adding chloropropionic acid chloride, the reaction temperature of the mixture was heated up to room temperature and stirred for 2 hours. After 30 g of active carbon was added and stirred still more, the active carbon was removed by filtration and filtrated solution was evaporated under a reduced pressure. The residue was recrystallized from water and thus 138 g (a yield of 60%) of compound (31-1) was obtained. 130 g of the compound (31-1) was dissolved in 800 ml of water and to this solution was added 222 g of sodium iodide. After then, the mixture was heated up to 60° C. and stirred for 3 hours. After the reaction, water was removed by evaporation under a reduced pressure. The residue was recrystallized from water and thus 139 g (a yield of 75%) of the exemplified Compound 31 was obtained and the chemical structure of thus obtained exemplified Compound 31 was confirmed by NMR and mass-spectrum thereof.

SYNTHETIC EXAMPLE 3
(Synthesis of an exemplified Compound 49)

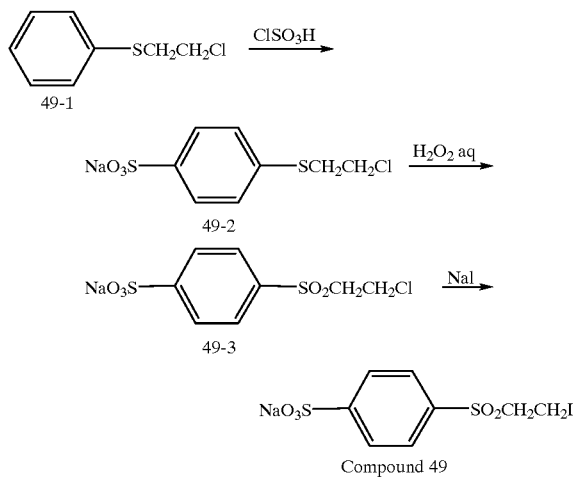

50 g of compound (49-1) was dissolved in 250 ml of dichloromathane and cooled at 5° C. By keeping the reaction temperature at 5° C., 54.0 g of chlorosurfuric acid was added little by little to the above obtained solution. After the mixture was stirred for 2 hours, the reaction temperature of the mixture was heated up to room temperature, then the reaction mixture was poured into 500 ml of a saturated solution of salt. By heating up and stirring thus obtained solution, then the solution was filtrated. The filtrated composition was washed with acetone and dried up, then 62 g (a yield of 84%) of compound (49-2) was obtained. Next, 57 g of the compound (49-2) was dissolved in 200 ml of water and to thus obtained solution was added 0.74 g of $Na_2WO_4 \cdot 2H_2O$, and the obtained mixture was cooled at 10° C. By keeping the reaction temperature at 10° C., 79 g of hydrogen peroxide aqueous solution was dropped to the reaction mixture. After the reaction, water was removed by evaporation under a reduced pressure. The residue was washed with acetone and dried up and then 52 g (a yield of 81%) of compound (49-3) was obtained. Further, 50 g of the compound (49-3) was dissolved in 400 ml of water and to thus obtained solution was added 109 g of sodium iodide. The reaction temperature was heated up to 65° C. and stirred. After the reaction, water was removed by evaporation under a reduced pressure and the residue was recrystallized from water and thus 55 g (a yield of 79%) of the exemplified Compound 49 was obtained and the chemical structure of thus obtained exemplified Compound 49 was confirmed by NMR and mass-spectrum thereof.

The iodide releasing compound of the present invention means the compound which can release an iodide ion under the basic condition and the example of base is cited a hydroxide ion, a hydroxylamine, an ammonium compound and an amine compound, but preferable one is an alkali hydroxide compound.

The process of preparing a silver halide photographic emulsion and a silver halide light sensitive photographic material generally comprise the steps of formation of silver halide grains, desalting, spectral sensitization, chemical sensitization, preparation of a coating solution, coating and drying. The iodide releasing compound of the present invention can be used at any step in the process of from the start of silver halide grain formation, thorough grain growth, physical ripening, desalting, spectral sensitization and chemical sensitization stages, to completion of the step of preparing a coating solution.

In the present invention, the silver halide grain formation is the stage from silver halide nucleus grain formation to completion of grain growth and physical ripening. The coating solution preparation is the stage from after completion of silver halide grain growth, physical ripening, and optionally desalting, spectral sensitization and chemical sensitization to the start of coating of a photographic material by the use of the silver halide emulsion related to the invention.

In this invention, the iodide ion releasing compound can be used at any step in the process of preparing a silver halide emulsion, preferably used at the step from after completing the formation of the vicinity of the outermost layer of the silver halide grain, that is, used at the step after from adding 90% of the amount of silver used for the formation of the silver halide grain and before the coating solution preparation.

In this invention, when the iodide ion releasing compound is added in the process of preparing a silver halide emulsion, the compound may be directly dispersed in an emulsion or dissolved in a single or mixed solvent, such as water, methanol or ethanol, and any method known in the art of adding an additive to a silver halide emulsion can be applicable.

In this invention, the iodide ion releasing compound can be added preferably in an amount of $1 \times 10^{-7}$ to 30 mol %, and more preferably $1 \times 10^{-6}$ to 5 mol % per mol of silver halide.

In this invention, according to the way of adding base, the concentration of base and reaction temperature, the iodide ion releasing timing or speed can be controlled.

In this invention, the concentration of the base is preferably $1 \times 10_{-7}$ to 50 mol, more preferably $1 \times 10^{-5}$ to 10 mol, and still more preferably $1 \times 10^{-3}$ to 5 mol. The temperature is preferably 20 to 90° C., more preferably 30 to 85° C., and still more preferably 35 to 80° C. In cases where a base is used for releasing a iodide ion, the pH may be controlled. The pH is preferably 2 to 12, and more preferably 3 to 11.

The iodide ion released is preferably 0.001 to 30 mol % and more preferably 0.01 to 10 mol % of total silver halide.

In this invention, the iodide ion releasing compound releases all or a part of iodide atom(s) contained in the compound. A part of the iodide ion releasing compound may remain without decomposition.

In this invention, the iodide ion releasing compound may be used singly or in combination of not less than 2 kinds.

The silver halide grains of the silver halide emulsion according to the invention preferably contain dislocation lines in the interior of the grain. The position of the dislocation lines is not limited, but the dislocation lines are present preferably in the vicinity of fringe portions, edges or corners of the grain. The dislocation lines are introduced into the silver halide grains preferably at not less than 50%, and more preferably not less than 60% and less than 85% of the total silver amount of silver halide grains. With respect to the number of dislocation lines, silver halide grains having 5 or more dislocation lines preferably account for at least 30%, more preferably at least 50%, and still more preferably at least 80%. The number of dislocation lines per grain is preferably not less than 10, more preferably not less than 20, and still more preferably not less than 30.

The dislocation lines of silver halide grains can be directly observed by means of transmission electron microscopy at a low temperature, for example, in accordance with methods described in J. F. Hamilton, Phot. Sci. Eng. 11 (1967) 57 and T. Shiozawa, Journal of the Society of Photographic Science and Technology of Japan, 35 (1972) 213. Silver halide grains are taken out from an emulsion while making sure not to exert any pressure that may cause dislocation in the grains, and they are then placed on a mesh for electron microscopy. The sample is observed by transmission electron microscopy, while being cooled to prevent the grain from being damaged by electron beam (e.g., printing-out). Since electron beam penetration is hampered as the grain thickness increases, sharper observations are obtained when using a high voltage type electron microscope. From the thus-obtained electron micrograph can be determined the position and number of the dislocation lines in each grain.

A method for introducing the dislocation lines into the silver halide grain is optional. An iodide (e.g., potassium iodide) aqueous solution is added along with a silver salt solution by a double jet technique, silver iodide fine grains are added, only an iodide solution is added, or a compound capable of releasing an iodide ion disclosed in JP-A (Japanese Patent Pulication Open to Public Inspection) No. 6-11781 is employed.

Any shape of the silver halide grain contained in the silver halide emulsion used in the present invention may be employed. For example, can be employed the grain having the regular crystal structure such as cubic form, an octahedral form and tetradecahedral form, or the grain having the irregular crystal structure such as spherical form or tabular form. Particularly, the tabular silver halide grain is preferably employed. Any of the area ratio of (100) face to (111) face constituting the silver halide grain surface of these grains can be used. Any combination usage of these silver halide grains can be used.

In this invention, an average particle diameter of the silver halide grain is preferable 0.2 to 10 μm, more preferable 0.3–7.0 μm, and especially preferable 0.4 to 5.0 μm.

The silver halide emulsion according to the invention may be optionally employed, such as a polydispersed emulsion with a wide diameter distribution and a monodispersed emulsion with a narrower diameter distribution, however, the monodispersed emulsion is preferred.

The silver halide emulsion according to the invention may be any one of conventionally used silver halide, such as silver iodobromide, silver iodochlorobromide or silver iodochloride, and silver iodobromide or silver iodochlorobromide is preferred.

The average silver iodide content of silver halide grains contained in the emulsion is preferably 1 to 40 mol %, and more preferably 2 to 20 mol %.

Silver halide grains contained in the silver halide emulsion according to the invention are preferably core/shell type grains. The core/shell type grains are those comprised of a core and a shell covering the core. The shell is formed of one or more layers. Silver iodide contents of the core and the shell preferably differ from each other.

The silver halide emulsion according to the invention can be prepared by various methods known in the art. Thus, the single jet addition, the double jet addition, the triple jet addition or the fine silver halide grain supplying method can be employed singly or in combination. Further, a method in which the pH and pAg in a liquid phase of forming silver halide grains are controlled in proportion to the growth rate of silver halide grains, is also employed in combination.

A seed grain emulsion can be employed to form the silver halide emulsion according to the invention. Silver halide grains of the seed emulsion may have a regular crystal structure such as cubic form, octahedral form and tetradecahedral form or an irregular crystal structure such as spherical or tabular form. The ratio of (100) face to (111) face of the grains is optional. The grains may be a composite of these crystal forms or a mixture of various crystal form grains. In this invention, in the case of using a tabular silver halide grain, the silver halide grains of the seed emulsion are preferably twinned crystal grains having at least one twin plane, and more preferably twinned crystal grains having two parallel twin planes.

In any cases where the seed emulsion is employed or not, methods known in the art can be applied to the conditions for silver halide nucleation and ripening.

Although a silver halide solvent known in the art may be employed in preparation of a silver halide emulsion. Examples of the silver halide solvent include (a) organic thioethers described in U.S. Pat. Nos. 3,217,157, 3,531,289, 3,574,628 and JP-A 54-1019, 54-158917 and JP-B (Examined Patent Pulication) 58-30571; (b) thiourea derivatives described in JP-A 53-82408, 55-29829 and 57-77736; (c) a silver halide solvent having a thiocarbonyl group interposing between a oxygen or sulfur atom and a nitrogen atom, described in JP-A 53-144319; (d) imidazoles described in JP-A 54-100717; (e) sulfites; (f) thiocyanates; (g) ammonia; (h) ethylendiamines substituted by a hydroxyalkyl group, described in JP-A 57-196228; (i) substituted mercaptotetrazoles described in JP-A 57-202531, (j) aqueous soluble bromides; and (k) benzimidazole derivatives described in JP-A 58-54333.

To prepare the silver halide emulsion of this invention can be applied any one of acidic precipitation, neutral precipitation and ammoniacal precipitation.

In preparation of the silver halide emulsion of the invention, a halide ion and a silver ion may be simultaneously added, or any one of them may be added into the other one. Taking into account the critical growth rate of silver halide crystals, the halide and silver ions can be added successively or simultaneously while controlling the pAg and pH within the reaction vessel. Halide composition of silver halide grains can be varied by a halide conversion method at any stage during the course of forming silver halide grains.

Using at least one selected from a cadmium salt, a zinc salt, a lead salt, thallium salt, a iridium salt (including its complex salt), a rhodium salt (including its complex salt), a iron salt or other VIII group metal salts (including their complex salts), a metal may be added to allow the metal to be occluded (or doped) in the interior and/or exterior of silver halide grains.

In this invention, the twinned crystal of silver halide grain having two opposing parallel twin planes can be used, but in this case the tabular silver halide grain is preferably employed. The above described twinned crystal is a silver halide crystal having at least one twin plane in one grain. The classification of the twin shapes is described in detail in Klein and Moiser, Photographisches Korrespondenz, Volume 99, page 99 and Volume 100, page 57. According to the invention tabular silver halide grains preferably account for at least 50%, more preferably at least 60%, and still more preferably at least 80% of the total projected area of silver halide grains contained in the emulsion.

In this invention, in the case of using the tabular silver halide grains, the tabular silver halide grains having two twin planes parallel to the major plane preferably account for at least 60%, more preferably at least 70%, and still more preferably at least 80%.

The ratio of grain diameter/thickness (aspect ratio) of the tabular silver halide grain employed in the present invention is not less than 1.3. The aspect ratio is preferably not less than 3.0, more preferably not less than 5.0.

To determine the aspect ratio, the diameter and the thickness of silver halide grains can be measured according to the following manner. Thus, a sample is prepared by coating on a support latex balls with a known diameter as a internal standard and silver halide grains so that the major faces are oriented in parallel to the support. After being subjected to shadowing from a given direction by the carbon vapor deposition method, a replica sample is prepared by a conventional replica method. From electronmicrographs of the sample, the projected area diameter and thickness can be determined using an image processing apparatus. In this case, the silver halide grain thickness can be determined from the internal standard and the length of shadow of the grain.

The twin plane of silver halide grains can be observed with a transmission electron microscope, for example, according to the following manner. A coating sample is prepared by coating a silver halide emulsion on a support so that the major faces of tabular silver halide grains are oriented substantially in parallel to the support. The sample is sliced by a diamond cutter to obtain an approximately. 0.1 $\mu$m thick slice. The presence of the twin plane can then be observed with a transmission electron microscope.

A dispersing medium in the silver halide emulsion according to the invention is a substance capable of forming a protective colloid, gelatin is preferably employed.

Gelatin used as the dispersing medium includes an alkali processed gelatin, an acid processed gelatin, and a deionized gelatin. Preparation of gelatin is described in detail in A. Veis, The Macromolecular Chemistry of Gelatin, Academic Press, 1964.

Examples of the protective colloid forming substance other than gelatin include gelatin derivatives, a graft polymer of gelatin and other polymers, proteins such as albumin or casein; cellulose derivatives such as hydroxyethyl cellulose, carboxymethyl cellulose and cellulose sulfuric acid ester; saccharide derivatives such as sodium alginate or starch derivatives; a synthetic or semi-synthetic hydrophilic polymer such as polyvinyl alcohol, polyvinyl alcohol partial acetal, poly-N-vinylpyrrolidone, polyacrylic acid, polyacrylamide, polyvinyl imidazole or polyvinyl pyrazole, including their copolymer. The silver halide emulsion according to the invention can be subjected to reduction sensitization using a method known in the art. The reduction sensitization may be performed during the stage of forming silver halide grains or after the grain formation.

Exemplary examples of the method of reduction sensitization include a method in which silver halide grains are ripened or grown at a low pAg by supplying silver ions (or so-called silver ripening), a method of ripening at a high pH by using an alkaline material and a method of adding a reducing agent. These reduction sensitization methods are employed optionally or in combination. Examples of the reducing agent include thiourea dioxide, ascorbic acid or its derivative, a stannous salt, a borane compound, a hydrazine derivative, formamidine sulfinic acid, silane compound, an amine or polyamine, and a sulfite. Of these, thiourea dioxide, ascorbic acid or its derivative or a stannous salt is preferably employed.

Known oxidizing agents can also be employed in the preparation of silver halide emulsions. Examples of the oxidizing agent include hydrogen peroxide (solution) or its adduct, such as $H_2O_2$, $NaBO_2$, $H_2O_2$—$3H_2O$, $2Na_2CO_3$—$3H_2O_2$, $Na_4P_2O_7$—$2H_2O_2$, and $2Na_2SO_4$—$H_2O_2$—$2H_2O$; peroxyacid salts such as $K_2S_2O_3$, $K_2C_2O_3$, $K_4P_2O_3$, $K_2[Ti(O)_2C_2O_4]$—$3H_2O$, peracetic acid, ozone and a thiosulfonic acid compound.

In preparing the silver halide emulsion of the invention, the reducing agent and the oxidizing agent can be employed in combination.

In cases where fine silver halide grains are employed in the invention, the fine silver halide grains may be prepared prior to or concurrently to the preparation of the silver halide emulsion according to the invention. When concurrently prepared, as described in JP-A 1-183417 and 2-44335, the fine silver halide grains can be prepared in a mixing vessel provided outside a reaction vessel in which silver halide emulsion relating to the invention is prepared. In this case, it is preferred that a preparation vessel is provided separately from the mixing vessel, a preparation vessel is provided, in which fine silver halide grains prepared in the mixing vessel is optimally prepared so as to be suitable for growth environment in the reaction vessel and then supplied to reaction vessel.

The fine silver halide grains are prepared preferably under an acidic or neutral environment (pH≦7).

The fine silver halide grains can be prepared by mixing a silver ion containing aqueous solution and a halide ion containing aqueous solution while optimally controlling supersaturation parameter(s). The control of the supersaturation parameter is referred to the description in JP-A 63-92942 and 63-311244.

To prevent production of reduced silver nuclei, the fine silver halide grains are prepared preferably at a pAg of not less than 3.0, more preferably not less than 5.0, and still more preferably not less than 8.0.

The fine silver halide grains are prepared preferably at a temperature of 50° C. or less, more preferably 40° C. or less, and still more preferably 35° C. or less.

As a protective colloid used in the preparation of the fine silver halide grains can be employed the afore-mentioned protective colloid forming substances used in the preparation of the silver halide emulsion according to the invention.

In the case when the fine silver halide grains are prepared at a low temperature, a grain size increase due to Ostwald ripening can be prevented but gelatin is liable to gel at a low temperature, so that a low molecular weight gelatin described in JP-A 2-166422, a synthetic polymer compound or a natural polymer compound other than gelatin, which has protective colloidal action onto silver halide grains, is preferably employed. The concentration of the protective colloid is preferably not less than 1% by weight, more preferably not less than 2%, and still more preferably 3%.

The diameter of the fine silver halide grains is preferably not more than 0.1 $\mu$m, and more preferably not more than 0.05 $\mu$m.

The fine silver halide grains may optionally be subjected to reduction sensitization or doped with a metal ion.

During or after forming silver halide grains, it is preferred to perform desalting to prevent physical ripening or remove unnecessary salts. Desalting can be carried out, for example, according to the method described in Research Disclosure (hereinafter, also denoted as "RD") 17643 Sect. II.

Thus, a noodle washing method by gelling gelatin or a flocculation method by the use of an inorganic salt, an anionic surfactant, an anionic polymer (e.g., polystyrene sulfonic acid) or a gelatin derivative (e.g., acylated gelatin, carbamoyled gelatin) is preferably employed to remove unnecessary salts from precipitates or a physical-ripened emulsion.

Desalting by employing membrane separation, as described in Kagaku Kogaku Binran (Handbook of Chemical Engineering) 5th Edition, page 924–954, edited by Kagakukogaku Kyokai and published by Maruzen.

The membrane separation method can further be referred to RD 10208 and 13122; JP-B 59-43727 and 62-27008; JP-A 57-209823, 59-43727, 61-219948, 62-23035, 62-113137, 63-40039, 63-40137, 2-172816, 2-172817, 3-140946 and 4-22942.

Conditions other than those described above can be optimally selected by reference to JP-A 61-6643, 61-14630, 61-112142, 62-157024, 62-18556, 63-92942, 63-151618, 63-163451, 63-220238 and 63-311244; RD 36544, 36736 and 39121.

A silver halide emulsion, which has been subjected to physical ripening, chemical sensitization and spectral sensitization, is employed to prepare the silver halide light sensitive photographic material according to the invention. Additives used in these processes are described in RD 17643, RD 18716 and RD 308119. Kinds of compounds described in these RD and described section are shown below.

| Additive | RD308119 Page Sec. | RD17643 | RD18716 |
| --- | --- | --- | --- |
| Chemical sensitizer | 996 III-A | 23 | 648 |
| Spectral sensitizer | 996 IV-A -A, B, C, D, H, I, J | 23–24 | 648–649 |
| Supersensitizer | 996 IV-A-E,J | 23–24 | 648–649 |
| Antifoggant | 998 VI | 24–25 | 649 |
| Stabilizer | 998 VI | 24–25 | 649 |

A known photographic additives are used to prepare the color photographic light-sensitive material using the silver halide emulsion according to the invention. Kinds of compounds described in these RD and described section are shown below.

| Additive | RD308119 Page Sec. | RD17643 | RD18716 |
| --- | --- | --- | --- |
| Anticolor-staining agent | 1002 VII-I | 25 | 650 |
| Dye stabilizer | 1001 VII-J | 25 | |
| Brightening agent | 998 V | 24 | |
| UV absorber | 1003 VIII, XIII-C | 25–26 | |
| Light absorber | 1003 VIII | 25–26 | |
| Antiirradiation dye | 1003 VIII | | |
| Filter dye | 1003 VIII | 25–26 | |
| Binder | 1003 IX | 26 | 651 |
| Antistatic agent | 1006 XIII | 27 | 650 |
| Hardener | 1004 X | 26 | 651 |
| Plasticizer | 1006 XII | 27 | 650 |
| Lubricant | 1006 XII | 27 | 650 |
| Surfactant | 1005 XI | 26–27 | 650 |
| Matting agent | 1007 XVI | | |
| Developing agent | 1011 XX-B | | |

Various couplers are used to prepare the color photographic light-sensitive material using the silver halide emulsion according to the invention. Kinds of couplers described in these RD and described section are shown below.

| Coupler | RD308119 Page Sec. | RD17643 |
| --- | --- | --- |
| Yellow coupler | 1001 VII-D | VII-C-G |
| Magenta coupler | 1001 VII-D | VII-C-G |
| Cyan coupler | 1001 VII-D | VII-C-G |
| Colored coupler | 1002 VII-G | VII-G |
| DIR coupler | 1001 VII-F | VII-F |
| BAR coupler | 1002 VII-F | |
| Other photographically useful agents releasing coupler | 1001 VII-F | |
| Alkali solubule coupler | 1001 VII-E | |

The additives used in the invention can be added by the dispersing method described in RD 308119 XIV. There are employed supports described in RD 17643 page 28, RD 18716 pages 647–648 and RD 308119 XIX.

The photographic material relating to the invention may be provided with an auxiliary layer such as a filter layer or interlayer. as described in RD 308119 VII-K.

As described in RD 308119 VII-K, the photographic material relating to the invention may have a layer arrangement, such as normal layer order, reversed layer order or unit constitution.

The present invention can be applied to a variety of color photographic materials, including a color negative film for general use or cine use, color reversal film for slide or television, color paper, color positive film, and color reversal paper.

The photographic material relating to the invention can be processed in accordance with conventional methods, as described in RD 17643 pages 28–29, RD 18716 page 615, and RD 308119 Sect. XIX.

EXAMPLES

The present invention is further explained based on examples, but embodiments of the present invention are by no means limited to these examples.

Example 1

Preparation of Seed Emulsion T-1

A seed grain emulsion, T-1 having two parallel twin planes was prepared according the following procedure.

E-1 Solution

| | |
| --- | --- |
| Deionized alkali-treated gelatin (Weight-averaged mean molecular weight 15,000) | 244.0 g |
| Potassium bromide | 156.6 g |
| 10% Surfactant (EO-1) methanol solution | 0.48 ml |
| Water to make | 34.0 l |

EO-1: $HO[(CH_2CH_2O)m(CH(CH_3)CH_2O]_{19.8}(CH_2CH_2O)nH-$ (m + n = 9.77)

F-1 Solution

| | |
| --- | --- |
| Silver nitrate | 1200 g |
| Water to make | 3716 ml |

G-1 Solution

| | |
| --- | --- |
| Deionized alkali-treated gelatin (Weight-averaged mean molecular weight 15,000) | 31.6 g |
| Potassium bromide | 906.0 g |
| Water to make | 4.0 l |

H-1 Solution

| | |
| --- | --- |
| Ammonia water (28%) | 299 ml |

-continued

| I-1 Solution | |
|---|---|
| Water | 8.0 l |
| J-1 Solution | |
| Ossein gelatin | 400.0 g |
| Water to make | 4832 ml |
| K-1 Solution | |
| Potassium bromide | 69.2 g |
| Water to make | 386 ml |
| L-1 Solution | |
| Aqueous 56 wt. % acetic acid solution | 1000 ml |

To solution E-1 with vigorously stirring at 30° C. by the use of a stirrer described in JP-A 62-160218 was added solution I-1 and then, solutions F-1 and G-1 were added by the double jet addition for a period of 2 min. to form silver halide nucleus grains.

Subsequently, solution J-1 was added thereto and after the temperature was raised to 68° C. in 41 min., solution H-1 was further added and ripening was carried out for 5 min. Then solution K-1 was added and after 1 min., the pH was adjusted to 4.7 with solution L-1 and the emulsion was immediately desalted. From electron microscopic observation of the resulting seed emulsion, it was proved that the was comprised of monodispersed silver halide seed grains having two parallel twin planes, an average grain diameter (equivalent circle diameter) of 0.31 μm and a grain diameter distribution of 16%.

Preparation of Em-1

Using the seed emulsion (T-1) and the following solutions was prepared a emulsion (Em-1).

| H-2 Solution | |
|---|---|
| Ossein gelatin | 223.6 g |
| 10% Surfactant (EO-1) methanol solution | 3.6 ml |
| Seed emulsion (T-1) | 0.774 mol equivalent |
| Water to make | 5904 ml |
| I-2 Solution | |
| 3.5N silver nitrate aqueous solution | 6490 ml |
| J-2 Solution | |
| 3.5N potassium bromide | 7500 ml |
| K-2 Solution | |
| Fine grain emulsion* comprised of 3.0 wt. % gelatin and fine silver bromide grains (average diameter of 0.05 μm) | necessary amount |

*Preparation of fine grain emulsion

To 5000 ml of a 6.0 wt. % gelatin aqueous solution containing 0.06 mol potassium iodide was added 2000 ml of an aqueous solution containing 7.06 mol silver nitrate and 2000 ml of an aqueous solution containing 7.06 mol potassium bromide at a constant flow rate for 10 min. During addition, the pH and temperature were maintained at 2.0 with nitric acid and at 40° C. After completing addition, the pH was adjusted to 6.0 with a sodium carbonate aqueous solution. Thus obtained fine grain emulsion was 12.53 Kg in weight.

| L-2 Solution | |
|---|---|
| 1.75N potassium bromide aqueous solution | necessary amount |
| M-2 Solution | |
| 56 wt. % acetic acid aqueous solution | necessary amount |
| N-2 Solution | |
| 3.5N potassium bromide | 500 ml |

To a reaction vessel was added solution H-2 and solutions I-2, J-2 and K-2 were added with vigorously stirring by the simultaneous addition method, as shown in Table 1, so that the seed grains were allowed to grow to obtain a core/shell type silver halide grain emulsion.

Herein, taking into account a critical growth rate, solutions I-2, J-2 and K-2 were added at an accelerated flow rate so that production of fine grains other than growing seed grains and widening of grain diameter distribution due to Ostwald ripening between growing grains did not occur.

Grain growth was performed in a manner such that the first addition was conducted, while the temperature and pAg of a solution within a reaction vessel were controlled at 75° C. and 8.8, respectively, thereafter, the temperature was lowered to 60° C. in 15 min and solution N-2 was added in 4 min. After solution K-2 was added in an amount of 2% of total used silver, and then the second addition was conducted while controlled at a temperature of 60° C., a pAg of 9.8 and a pH of 8.5. The pAg and pH were each controlled by adding solutions L-2 and M-2.

After completing grain formation, the emulsion was desalted according to the procedure described in JP-A 5-72658 and redispersed by adding gelatin thereto to obtain an emulsion with a pAg of 8.06 and a pH of 5.8 at 40° C.

From electron microscopic observation of silver halide emulsion grains, it was proved that the resulting emulsion was comprised of monodispersed, hexagonal tabular silver halide grains having an average diameter of 1.30 μm, a grain diameter distribution of 17% and an average aspect ratio of 8.0. The major plane was (111) plane and not less than 95% of the surface of total silver halide grains was composed of (111) plane. This tabular silver halide grains were shown to have dislocation lines.

TABLE 1

| Added solution | Adding time (min.) | Added amount of silver (%) | Molar ratio of iodide in halide solution | Adding division |
|---|---|---|---|---|
| | 0.00 | 0.0 | 8.5 | First addition |
| I-2 | 23.13 | 5.0 | 8.5 | |
| J-2 | 41.45 | 10.0 | 8.5 | |
| K-2 | 70.27 | 20.0 | 8.5 | |
| | 110.56 | 40.0 | 8.5 | |
| | 142.89 | 66.0 | 8.5 | |
| I-2 | 161.89 | 68.0 | 7.0 | Second addition |
| J-2 | 182.73 | 80.0 | 7.0 | |
| K-2 | 191.34 | 90.0 | 7.0 | |
| | 199.64 | 100.0 | 7.0 | |

Preparation of Em-2 to Em-14 and Em-29

Emulsion Em-2 to Em-14 and Em-29 were prepared in the same manner as emulsion Em-1, except that the compounds listed in Table 2 were added in an amount described in Table 2 of the total silver halide prior to desalting.

TABLE 2

| Emulsion No. | Compound | Added amount (× $10^{-4}$ mol%) | Remarks |
|---|---|---|---|
| Em-1 | — | — | Comparision |
| Em-2 | Comparative Compund 1 | 1 | Comparision |
| Em-3 | Comparative Compund 2 | 1 | Comparision |
| Em-4 | Comparative Compund 3 | 1 | Comparision |
| Em-5 | Inventive Compund 1 | 1 | Invention |
| Em-6 | Inventive Compund 3 | 1 | Invention |
| Em-7 | Inventive Compund 3 | 1.6 | Invention |
| Em-8 | Inventive Compund 21 | 1 | Invention |
| Em-9 | Inventive Compund 34 | 1 | Invention |
| Em-10 | Inventive Compund 45 | 1 | Invention |
| Em-11 | Inventive Compund 45 | 1.6 | Invention |
| Em-12 | Inventive Compund 49 | 1 | Invention |
| Em-13 | Inventive Compund 61 | 1 | Invention |
| Em-14 | Inventive Compund 61 | 1.6 | Invention |
| Em-29 | Comparative Compund 4 | 1 | Comparision |

These emulsions Em-2 to Em-14 and Em-29 were used after being subjected to optimal spectral and chemical sensitization.

On a subbed triacetyl cellulose film support were formed the following layers containing composition as shown below to prepare a multi-layered color photographic material Samples 101 to 114 and 129.

The addition amount of each compound was represented in term of g/m$_2$, provided that the amount of silver halide or colloidal silver was converted to the silver amount and the amount of a sensitizing dye (SD) was represented in mol/Ag mol.

| 1st Layer: Anti-Halation Layer | |
|---|---|
| Black colloidal silver | 0.16 |
| UV absorbent (UV-1) | 0.3 |
| Colored magenta coupler (CM-1) | 0.123 |
| Colored cyan coupler (CC-1) | 0.044 |
| High boiling solvent (OIL-1) | 0.167 |
| Gelatin | 1.33 |
| 2nd Layer: Intermediate Layer | |
| Anti-staining agent (AS-1) | 0.16 |
| High boiling solvent (OIL-1) | 0.20 |
| Gelatin | 0.69 |
| 3rd Layer: Low-speed Red-Sensitive Layer | |
| Silver iodobromide emulsion a | 0.20 |
| Silver iodobromide emulsion b | 0.29 |
| Sensitizing dye (SD-1) | $2.37 \times 10^{-5}$ |
| Sensitizing dye (SD-2) | $1.2 \times 10^{-4}$ |
| Sensitizing dye (SD-3) | $2.4 \times 10^{-4}$ |
| Sensitizing dye (SD-4) | $2.4 \times 10^{-6}$ |
| Cyan coupler (C-1) | 0.32 |
| Colored cyan coupler (CC-1) | 0.038 |
| High boiling solvent (OIL-2) | 0.28 |
| Anti-staining agent (AS-2) | 0.002 |
| Gelatin | 0.73 |
| 4th Layer: Medium-speed Red-sensitive Layer | |
| Silver iodobromide emulsion c | 0.10 |
| Silver iodobromide emulsion d | 0.86 |
| Sensitizing dye (SD-1) | $4.5 \times 10^{-5}$ |
| Sensitizing dye (SD-2) | $2.3 \times 10^{-4}$ |
| Sensitizing dye (SD-3) | $4.5 \times 10^{-4}$ |
| Cyan coupler (C-2) | 0.52 |
| Colored cyan coupler (CC-1) | 0.06 |
| DIR compound (DI-1) | 0.047 |
| High boiling solvent (OIL-2) | 0.46 |
| Anti-staining agent (AS-2) | 0.004 |
| Gelatin | 1.30 |
| 5th Layer: High-speed Red-Sensitive Layer | |
| Silver iodobromide emulsion c | 0.13 |
| Silver iodobromide emulsion d | 1.18 |
| Sensitizing dye (SD-1) | $3.0 \times 10^{-5}$ |
| Sensitizing dye (SD-2) | $1.5 \times 10^{-4}$ |
| Sensitizing dye (SD-3) | $3.0 \times 10^{-4}$ |
| Cyan coupler (C-2) | 0.047 |
| Cyan coupler (C-3) | 0.09 |
| Colored cyan coupler (CC-1) | 0.036 |
| DIR compound (DI-1) | 0.024 |
| High boiling solvent (OIL-2) | 0.27 |
| Anti-staining agent (AS-2) | 0.006 |
| Gelatin | 1.28 |
| 6th Layer: Intermediate Layer | |
| High boiling solvent (OIL-1) | 0.29 |
| Anti-staining agent (AS-1) | 0.23 |
| Gelatin | 1.00 |
| 7th Layer: Low-speed Green-Sensitive Layer | |
| Silver iodobromide emulsion a | 0.19 |
| Silver iodobromide emulsion b | 0.062 |
| Sensitizing dye (SD-4) | $3.6 \times 10^{-4}$ |
| Sensitizing dye (SD-5) | $3.6 \times 10^{-4}$ |
| Magenta coupler (M-1) | 0.18 |
| Colored magenta coupler (CM-1) | 0.033 |
| High boiling solvent (OIL-1) | 0.22 |
| Anti-staining agent (AS-2) | 0.002 |
| Anti-staining agent (AS-3) | 0.05 |
| Gelatin | 0.61 |
| 8th layer: Interlayer | |
| High boiling solvent (OIL-1) | 0.26 |
| Anti-staining agent (AS-1) | 0.054 |
| Gelatin | 0.61 |
| 9th Layer: Medium-speed Green-Sensitive Layer | |
| Silver iodobromide emulsion e | 0.54 |
| Silver iodobromide emulsion f | 0.54 |
| Sensitizing dye (SD-6) | $3.7 \times 10^{-4}$ |
| Sensitizing dye (SD-7) | $7.4 \times 10^{-5}$ |
| Sensitizing dye (SD-8) | $5.0 \times 10^{-5}$ |
| Magenta coupler (M-1) | 0.17 |
| Magenta coupler (M-2) | 0.33 |
| Colored cyan couple (CM-1) | 0.024 |
| Colored magenta coupler (CM-2) | 0.029 |
| DIR compound (DI-2) | 0.024 |
| DIR compound (DI-3) | 0.005 |
| High boiling solvent (OIL-1) | 0.73 |
| Anti-staining agent (AS-2) | 0.003 |
| Anti-staining agent (AS-3) | 0.035 |
| Gelatin | 1.80 |
| 10th Layer: High-speed Green-Sensitive Layer | |
| Em-1 | 1.19 |
| Sensitizing dye (SD-6) | $4.0 \times 10^{-4}$ |
| Sensitizing dye (SD-7) | $8.0 \times 10^{-5}$ |
| Sensitizing dye (SD-8) | $5.0 \times 10^{-5}$ |
| Magenta coupler (M-1) | 0.065 |
| Colored magenta coupler (CM-1) | 0.022 |
| Colored magenta coupler (CM-2) | 0.026 |
| DIR compound (DI-2) | 0.003 |
| DIR compound (DI-3) | 0.003 |
| High boiling solvent (OIL-1) | 0.19 |
| High boiling solvent (OIL-2) | 0.43 |

| -continued | |
|---|---|
| Anti-staining agent (AS-2) | 0.014 |
| Anti-staining agent (AS-3) | 0.017 |
| Gelatin | 1.23 |
| 11th Layer: Yellow Filter Layer | |
| Yellow colloidal silver | 0.05 |
| High boiling solvent (OIL-1) | 0.18 |
| Anti-staining agent (AS-1) | 0.16 |
| Gelatin | 1.00 |
| 12th Layer: Low-speed Blue-sensitive Layer | |
| Silver iodobromide emulsion a | 0.08 |
| Silver iodobromide emulsion b | 0.22 |
| Silver iodobromide emulsion h | 0.09 |
| Sensitizing dye (SD-9) | $6.5 \times 10^{-4}$ |
| Sensitizing dye (SD-10) | $2.5 \times 10^{-4}$ |
| Yellow coupler (Y-1) | 0.77 |
| DIR compound (DI-4) | 0.017 |
| High boiling solvent (OIL-1) | 0.31 |
| Anti-staining agent (AS-2) | 0.002 |
| Gelatin | 1.29 |
| 13th Layer: High-sped Blue-sensitive Layer | |
| Silver iodobromide emulsion h | 0.41 |
| Silver iodobromide emulsion i | 0.61 |
| Sensitizing dye (SD-9) | $4.4 \times 10^{-4}$ |
| Sensitizing dye (SD-10) | $1.5 \times 10^{-4}$ |
| Yellow coupler (Y-1) | 0.23 |
| High boiling solvent (OIL-1) | 0.10 |
| Anti-staining agent (AS-2) | 0.004 |
| Gelatin | 1.20 |
| 14th Layer: First Protective Layer | |
| Silver iodobromide emulsion j | 0.30 |
| UV absorbent (UV-1) | 0.055 |
| UV absorbent (UV-2) | 0.110 |
| High boiling solvent (OIL-2) | 0.30 |
| Gelatin | 1.32 |
| 15th Layer: Second protective Layer | |
| Polymer PM-1 | 0.15 |
| Polymer PM-2 | 0.04 |
| Lubricant (WAX-1) | 0.02 |
| Dye (D-1) | 0.001 |
| Gelatin | 0.55 |

Characteristics of silver iodobromide emulsions described above are shown below, in which the average grain size refers to an edge length of a cube having the same volume as that of the grain. The preparing method of the emulsions follows that of Em-1.

| Emulsion | Av. grain size ($\mu$m) | Av. AgI content (mol %) | Diameter/thickness ratio |
|---|---|---|---|
| a | 0.30 | 2.0 | 1.0 |
| b | 0.40 | 8.0 | 1.4 |
| c | 0.60 | 7.0 | 3.1 |
| d | 0.74 | 7.0 | 5.0 |
| e | 0.60 | 7.0 | 4.1 |
| f | 0.65 | 8.7 | 6.5 |
| h | 0.65 | 8.0 | 1.4 |
| i | 1.00 | 8.0 | 2.0 |
| j | 0.05 | 2.0 | 1.0 |

In addition to the above composition were added coating aids SU-1, SU-2 and SU-3; a dispersing aid SU-4; viscosity-adjusting agent V-1; stabilizers ST-1 and ST-2; fog restrainer AF-1 and AF-2 comprising two kinds polyvinyl pyrrolidone of weight-averaged molecular weights of 10,000 and 1,100,000; inhibitors AF-3, AF-4 and AF-5; hardener H-1 and H-2; and antiseptic Ase-1.

Chemical formulas of compounds used in the Samples described above are shown below.

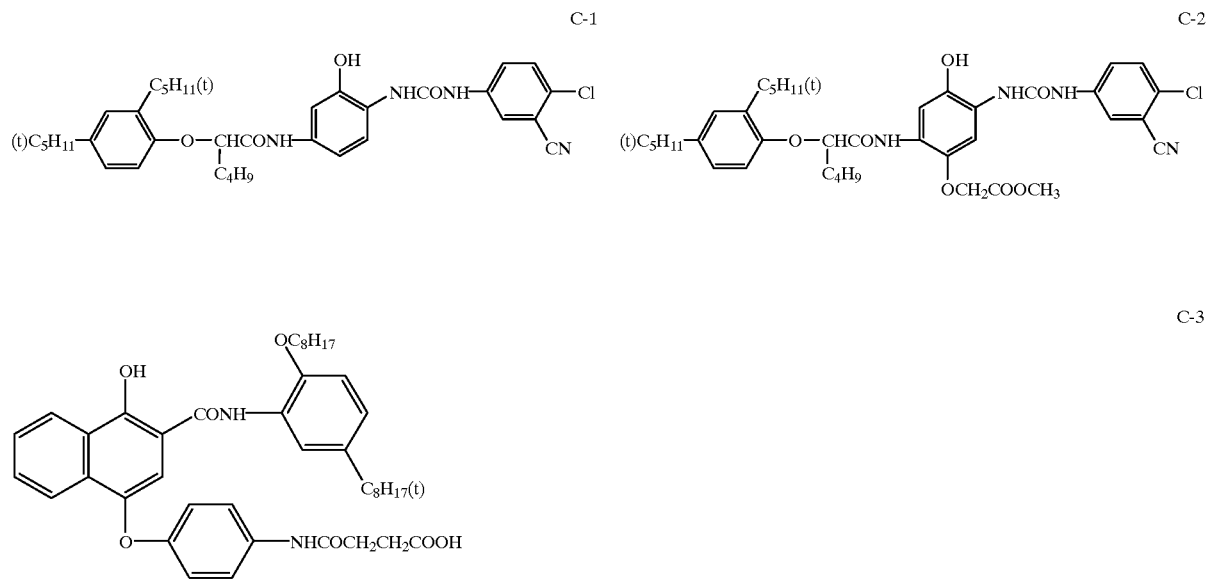

-continued
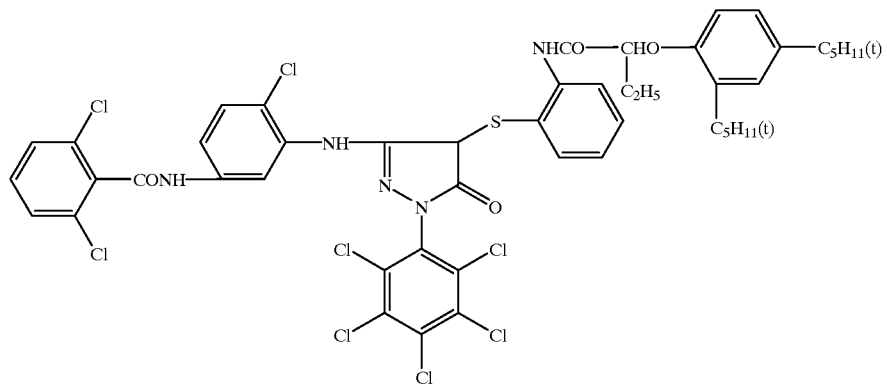
M-1
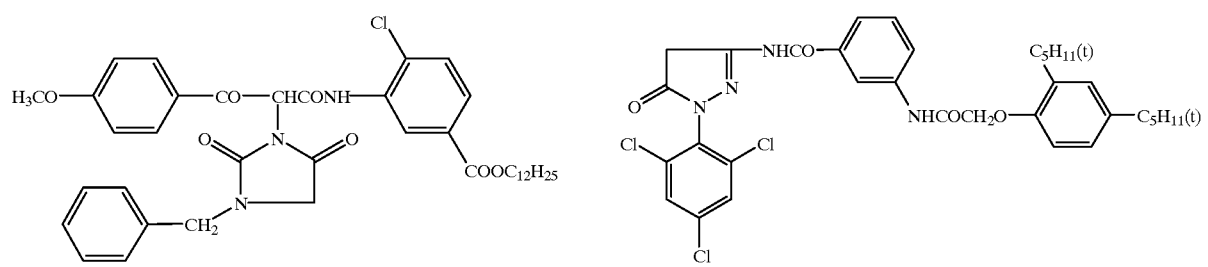
Y-1    M-2
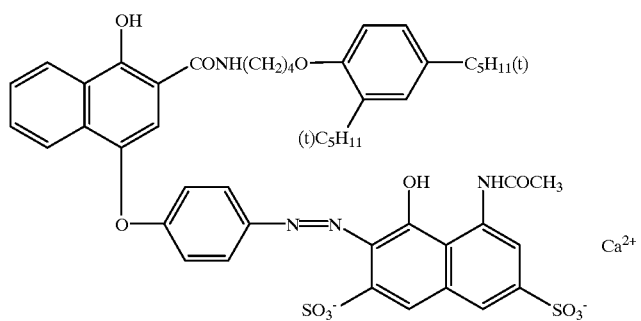
CC-1
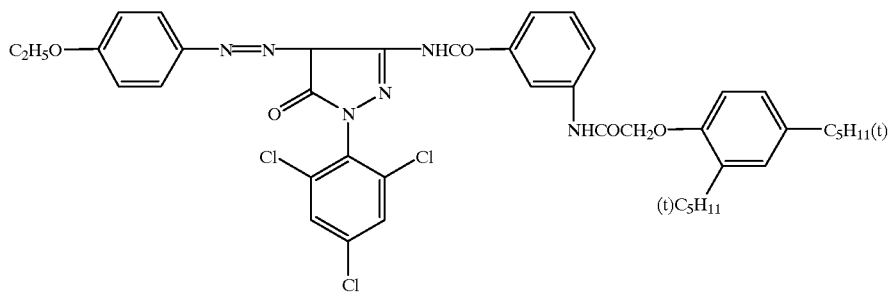
CM-1

CM-2
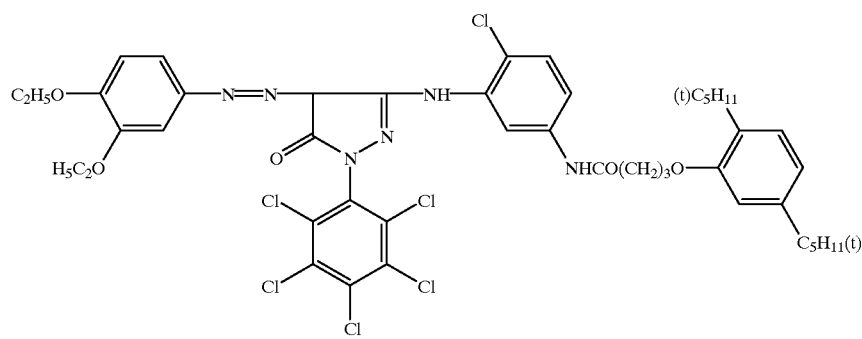
DI-1
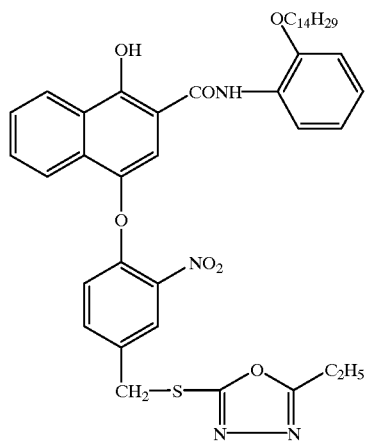
DI-2
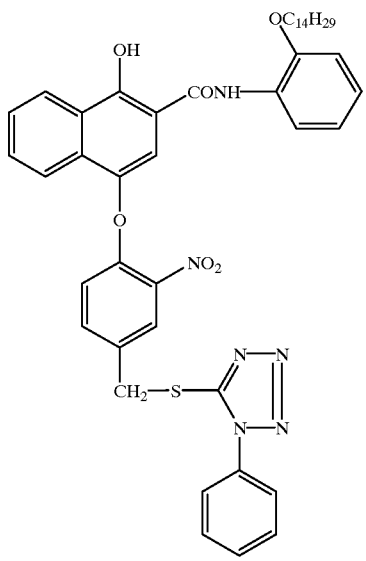
DI-3
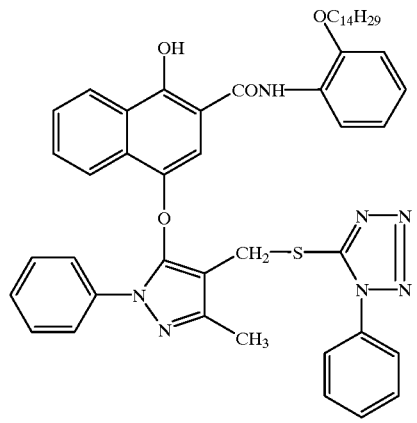
DI-4
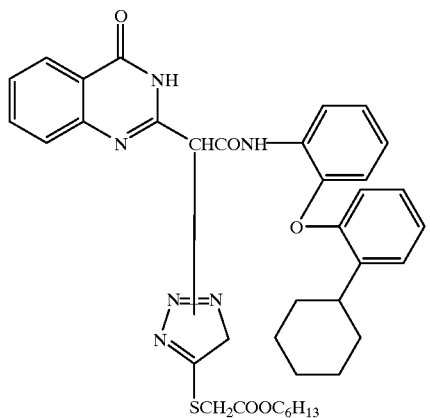
AS-1
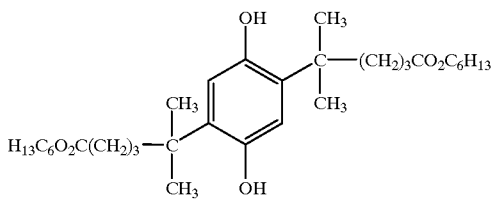
AS-2
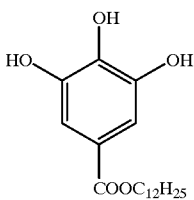

-continued
AS-3
SD-1
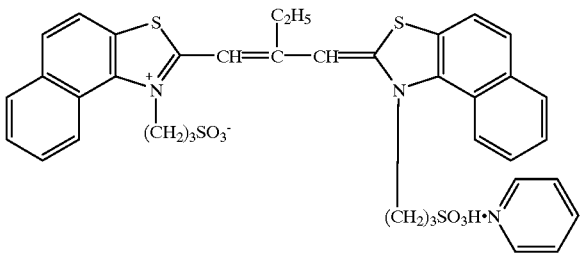
SD-2
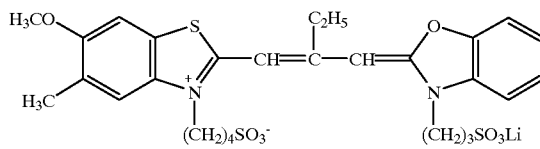
SD-3
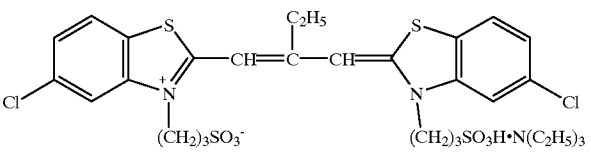
SD-4
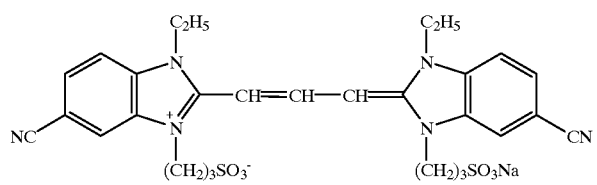
SD-5
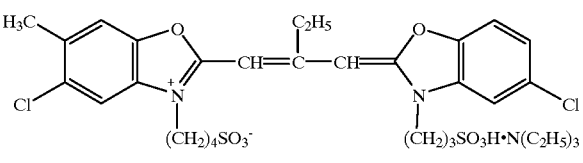
SD-6
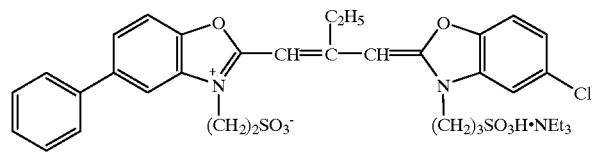
SD-7
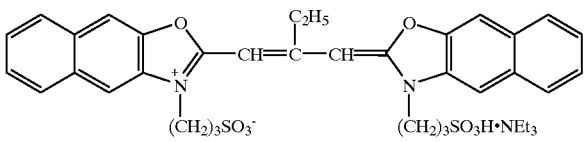
SD-8
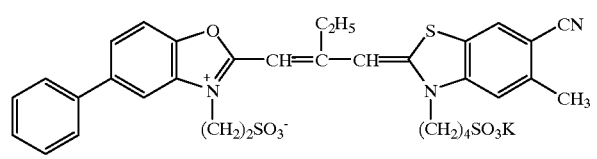
SD-9
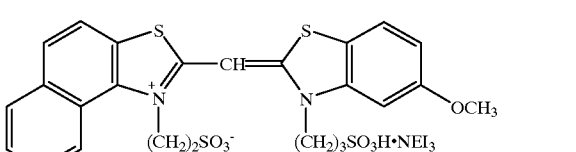
SD-10
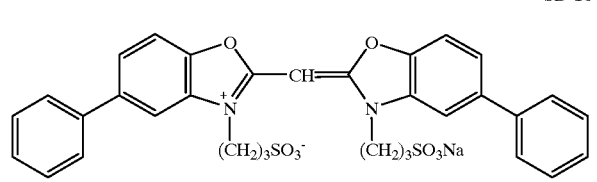
ST-1
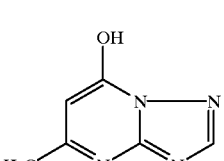
ST-2
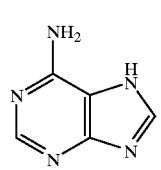
AF-1, 2
AF-1 Mw = 10,000
AF-2 Mw = 1,100,000
n: Polymerization degree
AF-3
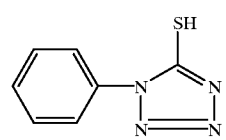
AF-4
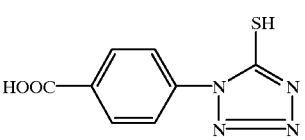

-continued
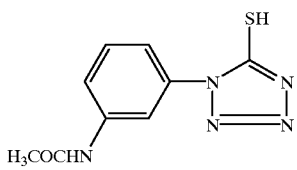
AF-5
$C_8F_{17}SO_2N(C_3H_7)-CH_2COOK$
SU-1
$C_8F_{17}SO_2NH(CH_2)_3N^+(CH_3)_3Br^-$
SU-2
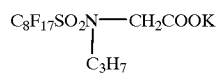
SU-3
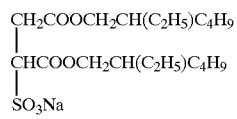
SU-4
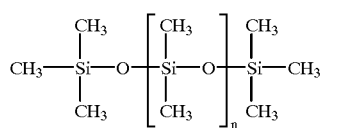
MW = 3,000
WAX-1
D-1
PM-1
x:y:z = 3:3:4
PM-2
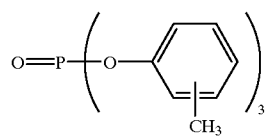
OIL-1
UV-1
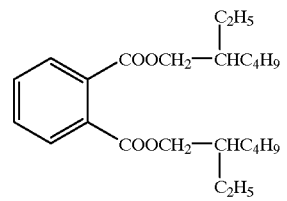
OIL-2

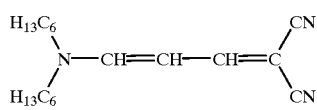

UV-2

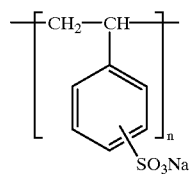

V-1 n: Polymerization degree

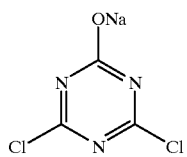

Ase-1 (Mixture)

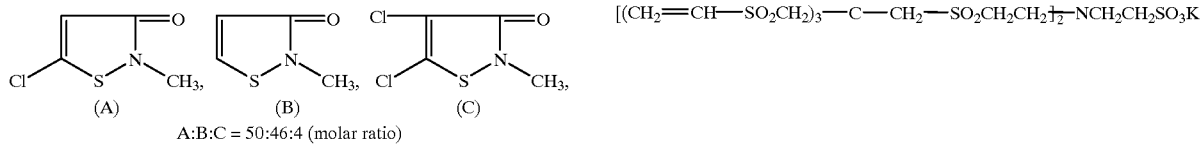

A:B:C = 50:46:4 (molar ratio)

H-1

[(CH$_2$=CH—SO$_2$CH$_2$)$_3$—C—CH$_2$—SO$_2$CH$_2$CH$_2$]$_{12}$—NCH$_2$CH$_2$SO$_3$K

H-2

Samples 101 to 114 were each processed according to the following procedure.

Processing:

| Processing step | Time | Temperature | Replenishing rate* |
|---|---|---|---|
| Color developing | 3 min. 15 sec. | 38 ± 0.3° C. | 780 ml |
| Bleaching | 45 sec. | 38 ± 2.0° C. | 150 ml |
| Fixing | 1 min. 30 sec. | 38 ± 2.0° C. | 830 ml |
| Stabilizing | 60 sec. | 38 ± 5.0° C. | 830 ml |
| Drying | 1 min. | 55 ± 5.0° C. | — |

*Amounts per m$^2$ of photographic material

A color developer, bleach, fixer and stabilizer each were prepared according to the following formulas.

Color developer and replenisher thereof:

| | Worker | Replenisher |
|---|---|---|
| Water | 800 ml | 800 ml |
| Potassium carbonate | 30 g | 35 g |
| Sodium hydrogencarbonate | 2.5 g | 3.0 g |
| Potassium sulfite | 3.0 g | 5.0 g |
| Sodium bromide | 1.3 g | 0.4 g |
| Potassium iodide | 1.2 mg | — |
| Hydroxylamine sulfate | 2.5 g | 3.1 g |
| Sodium chloride | 0.6 g | — |
| 4-Amino-3-methyl-N-(β-hydroxyethyl)-aniline sulfate | 4.5 g | 6.3 g |
| Diethylenetriaminepentaacetic acid | 3.0 g | 3.0 g |
| Potassium hydroxide | 1.2 g | 2.0 g |

Water was added to make 1 liter in total, and the pH of the developer and its replenisher were each adjusted to 10.06 and 10.18, respectively with potassium hydroxide and 20% sulfuric acid.

Bleach and replenisher thereof:

| | Worker | Replenisher |
|---|---|---|
| Water | 700 ml | 700 ml |
| Ammonium iron (III) 1,3-diamino-propanetetraacetic acid | 125 g | 175 g |
| Ethylenediaminetetraacetic acid | 2 g | 2 g |
| Sodium nitrate | 40 g | 50 g |
| Ammonium bromide | 150 g | 200 g |
| Glacial acetic acid | 40 g | 56 g |

Water was added to make 1 liter in total and the pH of the bleach and replenisher thereof were adjusted to 4.4 and 4.0, respectively, with ammoniacal water or glacial acetic acid.

Fixer and replenisher thereof:

| | Worker | Replenisher |
|---|---|---|
| Water | 800 ml | 800 ml |
| Ammonium thiocyanate | 120 g | 150 g |
| Ammonium thiosulfate | 150 g | 180 g |
| Sodium sulfite | 15 g | 20 g |
| Ethylenediaminetetraacetic acid | 2 g | 2 g |

Water was added to make 1 liter in total and the pH of the fixer and replenisher thereof were adjusted to 6.4 and 6.5, respectively, with ammoniacal water or glacial acetic acid.

Stabilizer and replenisher thereof:

| | |
|---|---|
| Water | 900 ml |
| p-Octylphenol/ethyleneoxide (10 mol) adduct | 2.0 g |
| Dimethylolurea | 0.5 g |
| Hexamethylenetetramine | 0.2 g |
| 1,2-benzoisothiazoline-3-one | 0.1 g |
| Siloxane (L-77, product by UCC) | 0.1 g |
| Ammoniacal water | 0.5 ml |

Water was added to make 1 liter in total and the pH thereof was adjusted to 8.5 with ammoniacal water or sulfuric acid (50%).

Samples 101 to 114 were exposed through an optical wedge, to white light at 3.2 CMS for 1/200 sec. and processed. From an obtained characteristic curve of each sample was determined a green sensitivity. Thus, the sensitivity was shown as a relative value of reciprocal of exposure necessary for giving a density of fog density plus 0.10 of a magenta density, based on the sensitivity of Sample 101 being 100.

Each sample was allowed to stand under the relative humidity of 80% at 40° C. for a week, thereafter each sample was similarly exposed and processed, then the sensitivity was evaluated based on the sensitivity of fresh Sample 101 being 100. The fog was also shown as a relative value based on the sensitivity of fresh Sample 101 being 100. Results thereof are shown in Table 3.

TABLE 3

| Sample No. | Emulsion No. | Sensitivity just after the sample prepared | Seneitivity after the sample reserved under 40° C., 80% RH for a week | Fog just after the sample prepared |
|---|---|---|---|---|
| 101 | Em-1 | 100 | 70 | 100 |
| 102 | Em-2 | 102 | 89 | 107 |
| 103 | Em-3 | 101 | 72 | 101 |
| 104 | Em-4 | 105 | 91 | 104 |
| 105 | Em-5 | 128 | 125 | 95 |
| 106 | Em-6 | 134 | 130 | 89 |
| 107 | Em-7 | 136 | 134 | 89 |
| 108 | Em-8 | 130 | 127 | 94 |
| 109 | Em-9 | 137 | 135 | 88 |
| 110 | Em-10 | 129 | 126 | 92 |
| 111 | Em-11 | 130 | 128 | 91 |
| 112 | Em-12 | 134 | 130 | 90 |
| 113 | Em-13 | 131 | 129 | 94 |
| 114 | Em-14 | 133 | 130 | 90 |
| 129 | Em-29 | 103 | 90 | 105 |

As is apparent from Table 3, Samples 105 to 114 in which inventive emulsions Em-5 to Em-14 were employed, exhibited superior sensitivity and lower fog to Samples 101 to 104 and 129 by the use of comparative emulsions Em-1 to Em-4 and Em-29.

Example 2

Preparation of Em-15 to Em-28 and Em-30

Emulsion Em-15 to Em-28 and Em-30 were prepared in the same manner as emulsion Em-1, except that the chemical sensitization was carried out by using the compounds listed in Table 4 being added in an amount described in Table 4 of the Total silver halide after the spectral sensitization.

TABLE 4

| Emulsion No. | Compound | Added amount ($\times 10^{-4}$ mol%) | Remarks |
|---|---|---|---|
| Em-15 | — | — | Comparision |
| Em-16 | Comparative Compund 1 | 2 | Comparision |
| Em-17 | Comparative Compund 2 | 2 | Comparision |
| Em-18 | Comparative Compund 3 | 2 | Comparision |
| Em-19 | Inventive Compund 2 | 2 | Invention |
| Em-20 | Inventive Compund 11 | 2 | Invention |

TABLE 4-continued

| Emulsion No. | Compound | Added amount ($\times 10^{-4}$ mol%) | Remarks |
|---|---|---|---|
| Em-21 | Inventive Compund 17 | 2 | Invention |
| Em-22 | Inventive Compund 24 | 2 | Invention |
| Em-23 | Inventive Compund 34 | 2 | Invention |
| Em-24 | Inventive Compund 41 | 2 | Invention |
| Em-25 | Inventive Compund 49 | 2 | Invention |
| Em-26 | Inventive Compund 63 | 2 | Invention |
| Em-27 | Inventive Compund 66 | 2 | Invention |
| Em-28 | Inventive Compund 95 | 2 | Invention |
| Em-30 | Comparative Compund 4 | 2 | Comparision |

Multilayered color photographic light-sensitive materials, Sample 201 to Sample 215 were provided in the same manner as Sample 101 except that in place of Em-1 in the tenth layer of Example 1, Em-15 to Em-28 and Em-30 were added in the tenth layer of Example 1 and evaluated. The fog was shown as a relative value based on the sensitivity of Sample 201 being 100. Results thereof are shown in Table 5.

TABLE 5

| Sample No. | Emulsion No. | Sensitivity just after the sample prepared | Seneitivity after the sample reserved under 40° C., 80% RH for a week | Fog just after the sample prepared |
|---|---|---|---|---|
| 201 | Em-15 | 100 | 71 | 100 |
| 202 | Em-16 | 102 | 88 | 108 |
| 203 | Em-17 | 101 | 74 | 102 |
| 204 | Em-18 | 109 | 98 | 105 |
| 205 | Em-19 | 128 | 124 | 95 |
| 206 | Em-20 | 127 | 124 | 94 |
| 207 | Em-21 | 129 | 126 | 94 |
| 208 | Em-22 | 130 | 126 | 92 |
| 209 | Em-23 | 138 | 135 | 89 |
| 210 | Em-24 | 132 | 129 | 91 |
| 211 | Em-25 | 137 | 134 | 88 |
| 212 | Em-26 | 131 | 127 | 92 |
| 213 | Em-27 | 128 | 125 | 95 |
| 214 | Em-28 | 127 | 125 | 94 |
| 215 | Em-30 | 106 | 85 | 106 |

As is apparent from Table 5, Samples 205 to 214 in which inventive emulsions Em-19 to Em-28 were employed, exhibited superior sensitivity and lower fog to Samples 101 to 104 and 215 by the use of comparative emulsions Em-15 to Em-18 and Em-30.

Example 3

The measurement of iodide releasing rate

The oxidation electric potential was measured in O Square Wave Voltammetry method by using 100B/Electrochemical Workstation (produced by BAS Co., Ltd.) and the iodide releasing rate was calculated. As a reference electrode was used Ag/AgCl electrode and as a working electrode was used fine gold electrode and as a counter electrode was used platinum electrode. Each compound was dissolved in sodium hydrogencarbonate/sodium carbonate buffering solution adjusted to pH 10.5 and the oxidation electric potential of each compound was measured at 42° C. in that solution. The iodide ion releasing rate was calculated from the ratio of the oxidation electric potential of each compound to the oxidation electric potential of potassium iodide. The iodide ion releasing rate was pursued with the passage of time. The measured and calculated results are shown in Table 6. In Table 6, time required for each compound to release 90% iodide ion from it is listed.

TABLE 6

| | Time required for the compound to release 90% iodide ion |
|---|---|
| Comparative Compound 1 | 12 min. |
| Comparative Compound 2 | *1 |
| Comparative Compound 3 | 20 min. |
| Comparative Compound 4 | 40 min. |
| Inventive Compound 1 | 3 min. |
| Inventive Compound 31 | 9 min. |
| Inventive Compound 49 | 0.5 min. |
| Inventive Compound 61 | 5 min. |

*1; Releasing ratio of iodide ion after 20 minutes was only 8%.

Comparative compound 1
$ICH_2CH_2OH$

Comparative compound 2

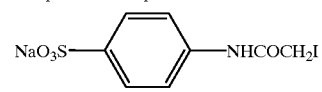

Comparative compound 3

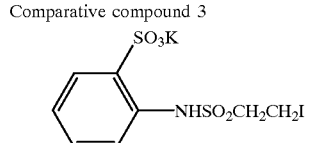

Comparative compound 4

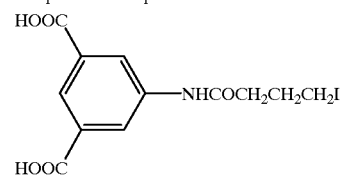

What is clamed is:

1. An iodide ion releasing compound represented by the following Formula [1],

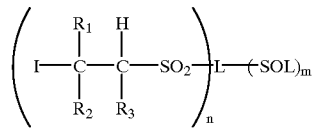

Formula [1]' wherein each of $R_1$, $R_2$ and $R_3$ represents a hydrogen atom or a substituent; L represents an aromatic group or a heterocyclic group; SOL represents aqueous soluble group; and each of n and m represents an integer of 1–4.

2. The iodide ion releasing compound of claim 1 wherein the iodide ion releasing compound is selected from the group consisting of 1)
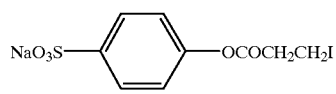

2)
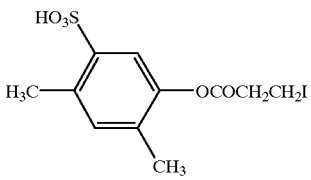

3)
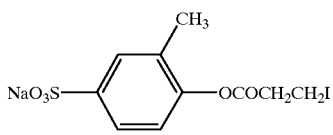

4)
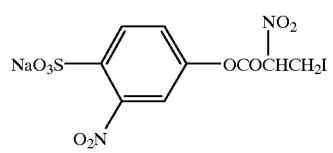

5)
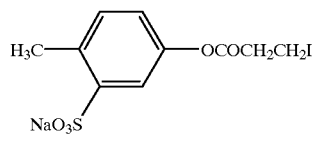

6)
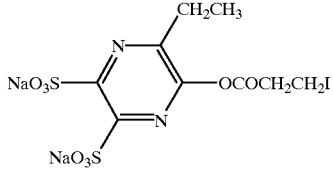

7)
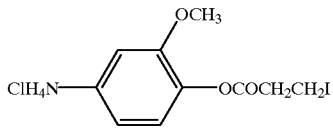

8)
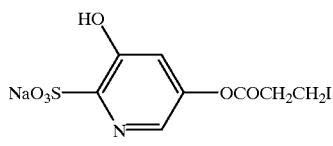

9)
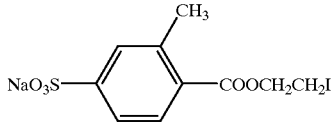

10)
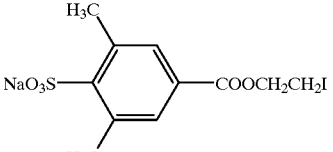

-continued

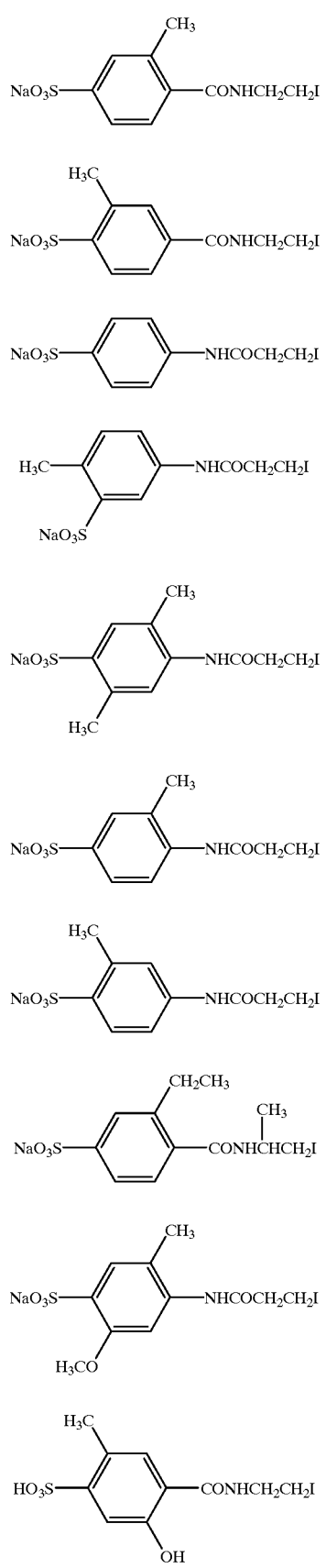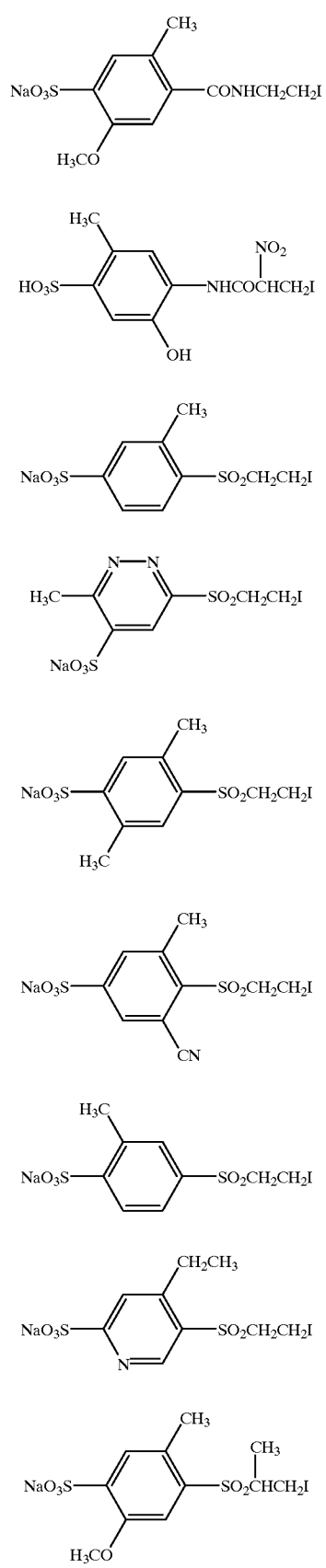

-continued
48)
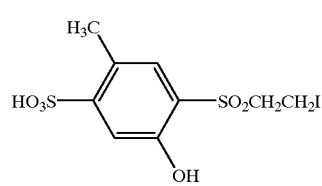
49)
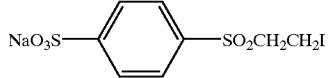
50)
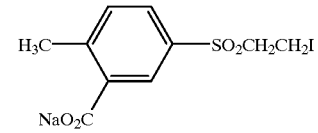
51)
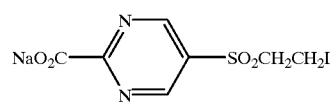
52)
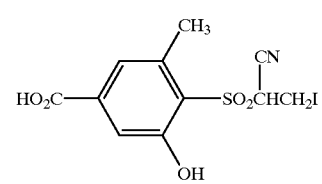
53)
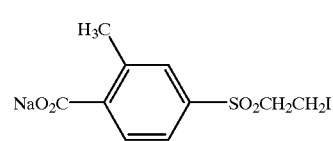
54)
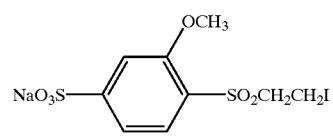
55)
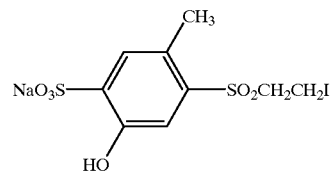
56)
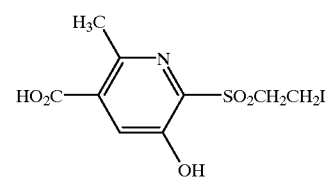
57)
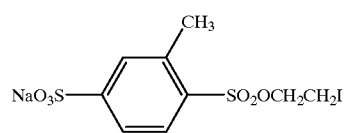
-continued
58)
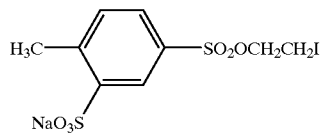
59)
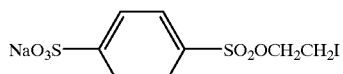
60)
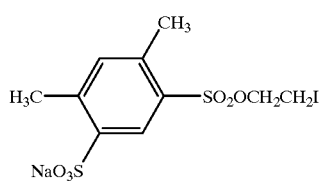
61)
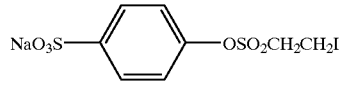
62)
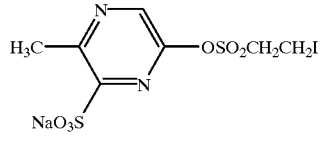
63)
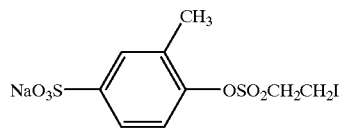
64)
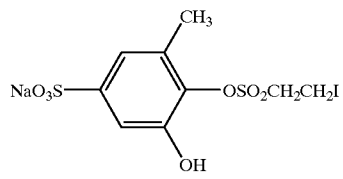
65)
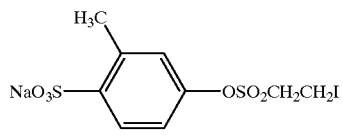
66)
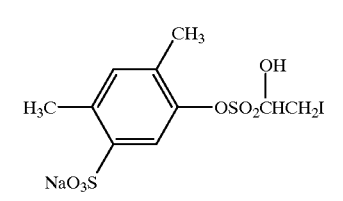
67)
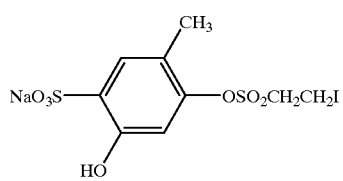

3. The iodide ion releasing compound of claim 2 wherein the iodide ion releasing compound is selected from the group consisting of 24)
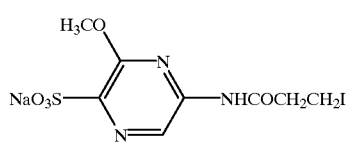

31)
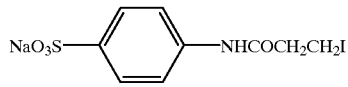

34)
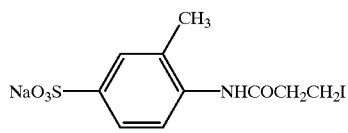

41)
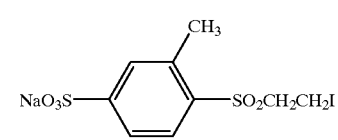

45)
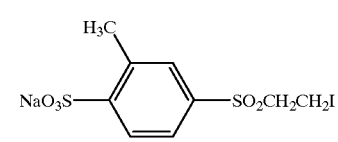

49)
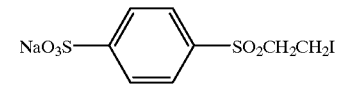

61)
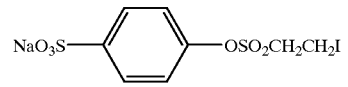

63)
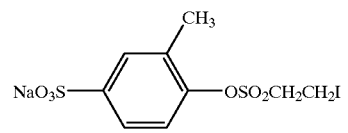

66)
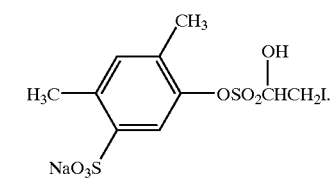

4. The iodide ion releasing compound of claim 3 wherein the iodide ion releasing compound is selected from the group consisting of 3)
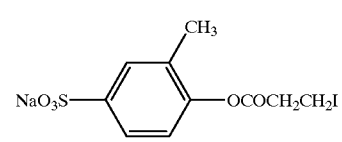

34)
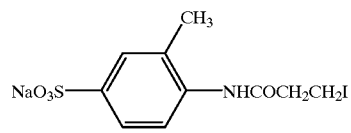

49)
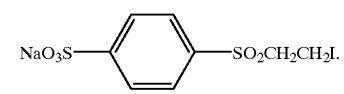

5. A silver halide grain formed using at least one of an iodide ion releasing compound represented by the following Formula [1],

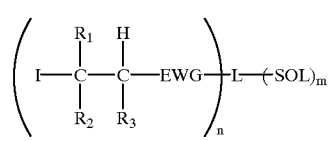

Formula [1]

wherein each of $R_1$, $R_2$ and $R_3$ represents a hydrogen atom or a substituent; EWG represents —$CO_2$—, —OCO—, —$SO_2$—, —$SO_2O$—, —$OSO_2$—, —$CONR_4$—, —$NR_5CO$—, —$CSNR_6$—, —$NR_7CS$—, —$NR_8$—, —O—, —S—, —CO—, —COCO— or —$NR_9SO_2$—; L represents an aromatic group or a heterocyclic group; SOL represents aqueous soluble group; $R_4$, $R_5$, $R_6$, $R_7$, $R_8$, and $R_9$ each represent a hydrogen atom or a substituent; and n and m each represents an integer of 1–4.

6. The silver halide grain of claim 5 wherein EWG represents —$SO_2$—.

7. A silver halide photographic light-sensitive material containing at least one of the silver halide grain formed using at least one of an iodide ion releasing compound represented by the following Formula [1],

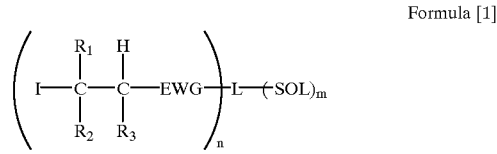

Formula [1]

wherein each of $R_1$, $R_2$ and $R_3$ represents a hydrogen atom or a substituent; EWG represents —$CO_2$—, —OCO—, —$SO_2$—, —$SO_2O$—, —$OS_2$—, —$CONR_4$—, —$NR_5CO$—, —$CSNR_6$—, —$NR_7CS$—, —$NR_8$—, —O—, —S—, —CO—, —COCO— or —$NR_9SO_2$—; L represents an aromatic group or a heterocyclic group; SOL represents aqueous soluble group; each of $R_4$, $R_5$, $R_6$, $R_7$, $R_8$, and $R_9$ represents a hydrogen atom or a substituent; and each of n and m represents an integer of 1–4.

8. The silver halide photographic material of claim 7 wherein EWG represents —$SO_2$—.

* * * * *